US011147282B2

(12) United States Patent
Omenetto et al.

(10) Patent No.: US 11,147,282 B2
(45) Date of Patent: *Oct. 19, 2021

(54) BIOPOLYMER-BASED PRESERVATION OF PERISHABLE PRODUCTS

(71) Applicant: Tufts University, Medford, MA (US)

(72) Inventors: Fiorenzo Omenetto, Lexington, MA (US); David Kaplan, Concord, MA (US); Benedetto Marelli, Somerville, MA (US); Mark Brenckle, Cambridge, MA (US)

(73) Assignee: Tufts University, Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/360,667

(22) Filed: Mar. 21, 2019

(65) Prior Publication Data

US 2019/0343137 A1 Nov. 14, 2019

Related U.S. Application Data

(63) Continuation of application No. 15/121,799, filed as application No. PCT/US2015/019163 on Mar. 6, 2015, now Pat. No. 10,271,561.

(60) Provisional application No. 61/949,995, filed on Mar. 7, 2014.

(51) Int. Cl.
| | |
|---|---|
| *A23B 7/16* | (2006.01) |
| *A01N 3/00* | (2006.01) |
| *A23L 3/3526* | (2006.01) |
| *C07K 14/435* | (2006.01) |
| *A23B 7/154* | (2006.01) |
| *A23L 3/3463* | (2006.01) |

(52) U.S. Cl.
CPC ............... *A23B 7/16* (2013.01); *A01N 3/00* (2013.01); *A23B 7/154* (2013.01); *A23L 3/3463* (2013.01); *A23L 3/3526* (2013.01); *C07K 14/43586* (2013.01); *A23V 2002/00* (2013.01)

(58) Field of Classification Search
CPC .. A23B 7/16; A23B 7/154; A01N 3/00; A23L 3/3463; A23L 3/3526; C07K 14/43586
USPC .......................................................... 426/89
See application file for complete search history.

(56) References Cited

U.S. PATENT DOCUMENTS

| | | | |
|---|---|---|---|
| 5,245,012 | A | 9/1993 | Lombari |
| 10,271,561 | B2 * | 4/2019 | Omenetto et al. |
| 2013/0243693 | A1 | 9/2013 | Omenetto |
| 2016/0281266 | A1 | 9/2016 | Omenetto |

FOREIGN PATENT DOCUMENTS

| | | |
|---|---|---|
| CN | 102796188 | 11/2012 |
| CN | 102870767 | 1/2013 |
| CN | 102870873 | 1/2013 |

(Continued)

OTHER PUBLICATIONS

Androjna, C. et al., Oxygen diffusion through natural extracellular matrices: implications for estimating "critical thickness" values in tendon tissue engineering, Tissue Engineering Part A, 14(4):559-569 (2008).

(Continued)

*Primary Examiner* — Helen F Heggestad
(74) *Attorney, Agent, or Firm* — Quarles & Brady, LLP

(57) ABSTRACT

Disclosed herein are biopolymer-based coatings and products incorporating such coatings. Related methods and use are also provided.

13 Claims, 13 Drawing Sheets

Specification includes a Sequence Listing.

(56) References Cited

FOREIGN PATENT DOCUMENTS

| | | |
|---|---|---|
| CN | 103200971 | 7/2013 |
| CN | 103223192 | 7/2013 |
| JP | H02113066 | 4/1990 |
| WO | 1997008315 | 3/1997 |
| WO | 1997023137 | 7/1997 |
| WO | 2008118211 | 10/2008 |
| WO | 2008127401 | 10/2008 |
| WO | 2008127402 | 10/2008 |
| WO | 2008127403 | 10/2008 |
| WO | 2008127404 | 10/2008 |
| WO | 2008140562 | 11/2008 |
| WO | 2009061823 | 5/2009 |
| WO | 2009155397 | 12/2009 |
| WO | 2010088585 | 8/2010 |
| WO | 2010126640 | 11/2010 |
| WO | 2011026101 | 3/2011 |
| WO | 2011046652 | 4/2011 |
| WO | 2011112931 | 9/2011 |
| WO | 2011130335 | 10/2011 |
| WO | 2012031144 | 3/2012 |
| WO | 2012031282 | 3/2012 |
| WO | 2012047682 | 4/2012 |
| WO | 2012054121 | 4/2012 |
| WO | 2013130156 | 9/2013 |

OTHER PUBLICATIONS

Cao, Z. et al., The preparation of regenerated silk fibroin microsphers, Soft Matter, 3:910-915 (2007).
China Patent Office Search Report for CN2015800217853, dated Mar. 11, 2019, 5 pages, machine translation.
Colombian Patent Office Office Action for NC2016/0002766, dated Nov. 9, 2016, 2 pages (original with translation).
Extended European Search Report and opinion for 15758977.1, dated Oct. 10, 2017, 6 pages.
Hu, X. et al., Regulation of silk material structure by temperature-controlled water vapor annealing, Biomacromolecules, 12(5):1686-1696 (2011).
International Preliminary Report on Patentability, PCT/US15/19163, 6 pages, dated Sep. 13, 2016.
International Search Report for PCT/US2015/019163, 3 pages (dated May 25, 2015).
Jin, H.J. et al., Water-stable silk films with reduced beta-sheet content, Advanced Functional Materials, 15:1241-1247 (2005).
Ku, K.J. et al., Preparation of a Silk Fibroin Film Containing Catechin and Its Application, Food Science and Biotechnology, 17(6):1203-1206 (2008).
Lucas, F. et al., The silk fibroins, Advanced Protein Chemistry, 13:107-242 (1958).
Matsumoto, A. et al., Silk fibroin solution properties related to assembly and structure, Macromolecular Bioscience, 8(11):1006-1018 (2008).
Omenetto, F.G. and Kaplan, D.L., New opportunities for an ancient material, Science, 329(5991):528-531 (2010).
Ribeiro, C. et al., Optimization of edible coating composition to retard strawberry fruit senescence, Postharvest Biology and Technology, 44:63-70 (2007).
Rockwood, D.N. et al., Materials fabrication from Bombyx mori silk fibroin, Nature Protocols, 6(10):1612-1631 (2011).
Saengthong, Salita, et al. "Fabrication of microporous chitosan/silk fibroin as a scaffold material using electron beam." Macromolecular Research 22.7 (2014): 717-724.
Valentin, J.E. et al., Oxygen diffusivity of biologic and synthetic scaffold materials for tissue engineering, Journal of Biomedical Materials Research, 91A(4):1010-1017 (2009).
Velickova, E. et al., Impact of chitosan-beeswax edible coatings on the quality of fresh strawberries, Food Science and Technology, 52:80-92 (2013).
Wang, Y. et al., Nanoscale Characterization of Zein Self-Assembly, Langmuir, 28(5):2429-2435 (2012).
Written Opinion for PCT/US2015/019163, 5 pages (dated May 25, 2015).

\* cited by examiner

BIOPOLYMER-BASED PRESERVATION OF PERISHABLE PRODUCTS

CROSS-REFERENCE TO RELATED APPLICATIONS

This application is a continuation application of U.S. Ser. No. 15/121,799 filed Aug. 26, 2016, which represents the national stage entry of PCT/US2015/019163, filed Mar. 6, 2015, which claims benefit of U.S. Provisional Patent Application 61/949,995 filed Mar. 7, 2014. The contents of these applications are hereby incorporated by reference as set forth in their entirety herein.

GOVERNMENT SUPPORT

This invention was made with government support under grant number FA9550-10-1-0172 awarded by the United States Air Force and grant number N00014-13-1-0596 awarded by the United States Navy. The government has certain rights in the invention.

BACKGROUND

Preservation of perishable goods, food in particular, typically involves preventing the growth of bacteria, fungi (such as yeasts), and other micro-organisms, as well as retarding the oxidation of fats that cause rancidity. Food preservation can also involve inhibiting enzymatic processes, which lead to discoloration and/or changes in texture of the perishable goods. In addition to or concurrent with visual deterioration, maintaining nutritional value and flavor is also an important aspect of food preservation.

There are a number of techniques that have been traditionally used to enhance preservation of perishable items. These include, for example, drying, pasteurization, refrigeration, freezing, vacuum packing, salting or curing, sugaring, smoking, chemical additives, pickling, lye, canning and bottling, irradiation, etc.

More recently, food coating (sometimes referred to as glazing) has been exploited as a means of enhancing preservation, as well as organoleptic properties. Several classes of biopolymers have been contemplated as coating materials: polysaccharides, proteins, lipids, as well as various combinations of these biopolymers (reviewed, for, example, in: *Biopolymers—New Materials for Sustainable Films and Coatings*. Copyright (©) 2011 John Wiley & Sons, Ltd., Editor(s): David Plackett; Print ISBN: 9780470683415; Online ISBN: 9781119994312; CH. 10 "Food Packaging Applications of Biopolymer-Based Films"; CH. 11 "Biopolymers for Edible Films and Coatings in Food Applications"; contents of which are incorporated herein by reference). Polysaccharides and proteins are known to form films with good mechanical properties, but with poor permeability, while the lipids form brittle films but with improved permeability. Coating fruits and vegetables with a waxing material is also a common example. The primary reasons for waxing are to prevent water loss and thus retard shrinkage and spoilage, and to improve appearance. The waxing materials used for such purposes depend to some extent on regulations in the country of production and/or export; both natural waxes (e.g., sugar-cane, carnauba, shellac, and resin) and petroleum-based waxes are used. Wax may be applied in a volatile petroleum-based solvent but is now more commonly applied via a water-based emulsion. Blended paraffin waxes applied as an oil or paste are often used on vegetables. Such techniques are useful for selective products, but not for others.

SUMMARY OF THE INVENTION

The present invention provides, among other things, biopolymer-based compositions and methods for the preservation of perishable goods, including food. In particular, the invention includes the recognition that certain biopolymers offer structural features that are particularly suited for the production of coating materials for perishable products, without the requirement of added plasticizer to achieve desirable malleability. Accordingly, described herein are safe, simple, and versatile coatings that enhance preservation of various perishable products.

In some embodiments, biopolymer-based coating materials used to preserve the perishables are useful for forming a barrier between a perishable item and one or more elements in its environment. In some embodiments, such coating materials provide a selective barrier between the perishable item and at least one aspect of its environment. For example, such materials provide a selective barrier between the perishable item and at least one aspects of its environment, such as light (e.g., certain ranges of wavelengths of light), temperature, moisture or water contents, microbes (e.g., bacteria, fungi, etc.), and so on.

The invention also encompasses the notion that biopolymer-based coatings described herein may be used as a carrier for one or more agents. In some embodiments, such coatings incorporate an agent or agents to further enhance preservation of a perishable item. Examples include, without limitation, enzyme inhibitors, anti-microbe agents, and ethylene-capturing agents.

Additionally or alternatively, in some embodiments, such coatings carry an agent or agents that are used for purposes other than for enhanced preservation of a perishable item. For example, such coatings may incorporate an agent or agents to provide additional attribute(s) or feature(s), including, without limitation, added or improved taste or flavor, appearance, nutritional contents, scents, etc. In some embodiments, additional agents may provide functionality, such as labeling or coding that carries certain information. Any suitable or desirable information may be encoded or included, including, without limitation, identification information, such as information about the source or origin of a product, ingredients, nutritional information, manufacturing information, processing dates (date of harvest, date of coating or packaging, etc.), expiration dates, pricing information, authentication, advertisement, customer service information, or any combination thereof.

In some embodiments, biopolymer-based coatings described herein can enhance one or more feature of a perishable product. For example, such coatings may provide enhanced appearance (e.g., color, shine/gloss, etc.), enhanced texture (e.g., crispness, etc.) and so on.

In some embodiments, biopolymer-based coating materials used to preserve the perishables are applied directly to adhere to the surface of a perishable item.

In some embodiments, biopolymer-based coating materials used to preserve the perishables provide packaging for perishable items.

In some embodiments, biopolymer-based coating materials used to preserve the perishables form an edible coating of a perishable item, e.g., food. In some embodiments, such coating materials need not be washed off prior to consumption. In some embodiments, such coating materials may be washed away, for example with water, prior to consumption.

In some embodiments, biopolymer-based edible coatings described herein do not affect the taste, flavor and/or appearance of the perishable food coated therewith. In some embodiments, such biopolymer-based edible coatings described herein do not negatively affect the taste, flavor and/or appearance of the perishable food coated therewith.

BRIEF DESCRIPTION OF THE DRAWING

FIGS. 4A-4C show at panel (a) wicking; (b) hydrodynamic permeability; and, (c) diffusivity of water. For wicking study, silk fibroin crystalline membranes (thickness=130 μm) showed wicking of dyed water in Z and XY direction, indicating the capillary diffusion of water through silk fibroin thin constructs. Investigation of hydrodynamic permeability showed no statistically relevant effect ($p>0.05$) of silk fibroin crystallinity on water permeation (as per one way ANOVA test with Tukey mean analysis). The study of water diffusivity revealed that crystallinity of silk membranes slightly affected mass transport of water through silk (as per one way ANOVA test with Tukey mean analysis).

FIG. 5A shows time lapse photography of banana ripening indicating that silk coating decreased the ripening rate. FIG. 5B shows investigation of silk-coated banana turgidity (i) when compared to uncoated control (ii). The test was accomplished ad day 9 after coating. Silk-coated banana showed an increased firmness, when compared to uncoated control. FIG. 5C shows photography of the internal flesh of non-coated (i) and coated (ii) bananas at day 9 post silk coating-treatment. Flesh of non-coated banana presented a brown color, while silk-coated fruits preserved a tallow flesh, indication of a decreased ripening rate within the silk-coated sample.

FIG. 7A shows the impact of silk fibroin edible coating was investigated on freshly picked strawberries. FIG. 7A at panel (i) shows silk fibroin was extracted from *Bombyx mori* cocoon fibers by dissolution in 9.3 M LiBr solution and FIG. 7A at panel (ii) dialysis in deionized water. The concentration of the protein in water was then adjusted to 1 wt %. FIG. 7A at panel (iii) shows coating of strawberries was then achieved by dip coating process in silk fibroin solution (1 wt %). The dip coating process was repeated up to 4 times. FIG. 7A at panel (iv) shows crystallinity of the silk fibroin edible coating was modulated using water annealing post-processing. The longer the exposure to water vapor (up to 12 hours), the higher the crystallinity degree of the protein. FIG. 7A at panel (v) shows silk fibroin-coated strawberries were then left at room conditions (T=22° C., RH=38%) to investigate the impact of the edible coating on the quality of the fruit. Crystal violet dye was used to stain the silk fibroin coating. FIG. 7B shows representative macroscopic images of stained strawberries. FIG. 7B at panel (i) shows freshly picked, FIG. 7B at panel (ii) shows coated with an amorphous silk fibroin edible coating (4 dip coating processes, no water annealing applied), and FIG. 7B at panel (iii) shows coated with a crystalline silk fibroin edible coating (4 dip coating processes, 12 hours of water annealing). The crystal violet dye is barely visible on the surface of the coated strawberries (black dots) due to the few-micron thickness of the coating. FIG. 7C shows stereoscopic images of the surface and of the cross-section (insets) of crystal violet-stained fresh strawberries FIG. 7C at panel (c)(i) shows as picked, FIG. 7C at panel (c) shows coated with an amorphous silk fibroin edible coating, and FIG. 7C at panel (c) shows coated with a crystalline silk fibroin edible coating. Scale bars: 2 mm.

FIG. 8A shows time-lapse of strawberries ripening. As picked strawberries were stored at 22° C. and 38% RH (no coating) or dip coated in silk fibroin solution (amorphous silk coating). Water annealing was used as post-process to modulate silk fibroin crystallinity degree. At day 7, crystalline silk fibroin coating only showed to improve the quality of the stored strawberries. FIG. 8B shows weight loss of strawberries stored for up to 14 days at 22° C. and 38% RH. Strawberries were stored as picked (i.e. no coating) or after coating with silk fibroin solution (DxCx). Dx stands for 'x' dip coating steps. Cx stands for 'x' hours of water annealing post-process (e.g. D1C0 means that strawberries were dip coated once and that were not exposed to water annealing). Two-ways ANOVA test with Tukey mean analysis was used to evaluate the weight loss data. Silk crystallinity but not number of dip coating steps affected the dehydration of the strawberries considered. No coating controls lost circa 70 wt % of their original weights in the 14 days considered (highlighted within the red rectangles). Strawberries coated with amorphous silk (DxCO) retained more water than the no coating controls at day 3 (p<0.05). Crystalline silk fibroin coating further slowed fruit dehydration compared to amorphous silk fibroin coating (p<0.05) and to the no coating control (p<0.05) but no statistical difference was found for different time of water annealing (p>0.05).

FIGS. 9A-9E show permeability and diffusivity of water and oxygen in silk fibroin films as a function of protein crystallinity and their effects on the quality of the edible coating. FIG. 9A shows hydrodynamic permeability of silk fibroin films. The crystallinity degree of the protein does not affect the leakage of water through the film (p<0.05). FIG. 9B shows diffusivity of water in silk fibroin films. The crystallinity degree of the protein affects the diffusivity of water in the transient state (0<t<25 minutes) but not in the steady state (t>25 minutes). FIG. 9C shows oxygen diffusion in silk fibroin films. Silk fibroin polymorphism strongly affects oxygen diffusion as a 50 fold decreased in the effective diffusion coefficient of oxygen was measured between an amorphous and a highly crystalline silk fibroin film. FIG. 9D shows respiration rate of silk-coated strawberries was measured as a function of coating crystallinity, where higher crystallinity degrees corresponded a statistically significant decrease in the production of $CO_2$ (p<0.05). FIG. 9E shows effects of silk coating on the firmness of strawberries as a function of storage time and of coating crystallinity. Natural decay of the strawberries causes a decrease in the fruit firmness, as measure by a time-dependent decrease in the force required to penetrate the fruit (p<0.05). An increase in the coating crystallinity corresponded to a statistically significant delay in the decay of the fruit firmness at days 3 and 7.

FIG. 10A shows time lapse photography of banana ripening indicating that silk coating decreased the ripening rate. FIG. 10B shows an investigation of silk-coated banana turgidity. FIG. 10B at panel (i) shows turgidity of an uncoated control. Turgidity was studied qualitatively by applying a dead load (200 g) on the surface of the fruit. FIG. 10B at panel (ii) shows the test was accomplished at day 9 after coating. Silk-coated banana showed an increased firmness, when compared to uncoated control. FIG. 10C at panel (i) shows images of the internal flesh of a non-coated banana and FIG. 10C at panel (ii) shows images of the internal flesh of a coated banana at day 9 post silk coating-treatment. Flesh of non-coated banana presented a brown color, while silk-coated fruits preserved a tallow flesh, indication of a decreased ripening rate for the silk-coated samples.

DETAILED DESCRIPTION OF CERTAIN EMBODIMENTS

Figure 1:
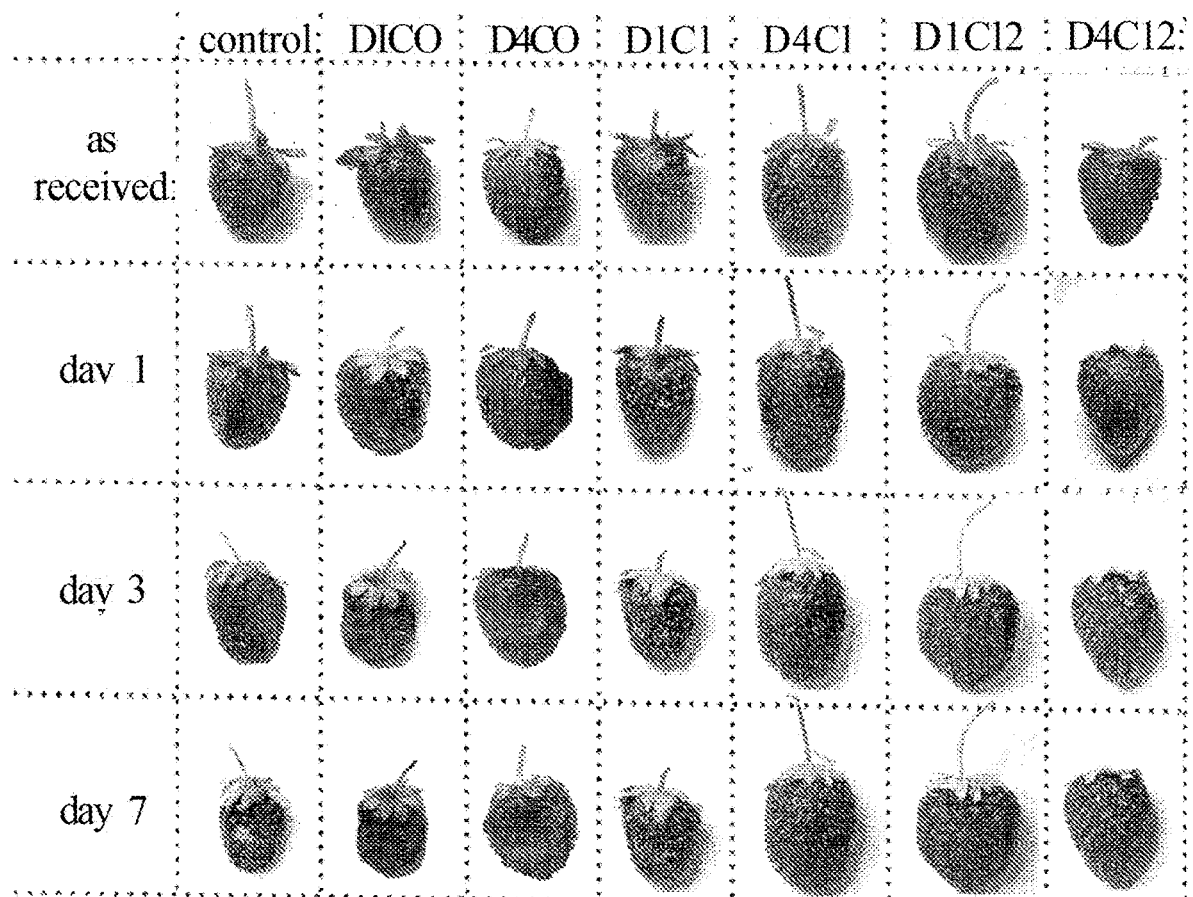
FIG. 1 provides time-lapse images of the aging process of berries. Berries were stored at 22° C. and 38% RH as received (control) and after coating with silk fibroin solution (DxCx). Dx stands for 'x' dip coating steps. Cx stands for 'x' hours of water annealing. Thus, D1C0 means strawberries that were dip coated only once and that were not exposed to water annealing.

The present disclosure provides biopolymer-based edible coatings suitable for coating perishable products, such as food items. Among other things, the present invention encompasses protein-based (i.e., polypeptide-based) coating materials and related methods that do not require the use of added plasticizers. Certain desirable material and physiochemical characteristics of such proteins (i.e., peptides) are described in more detail below. Coatings prepared in accordance with the present invention show superior ability to preserve the perishable such as fresh fruits, as compared to known edible coatings. Furthermore, such coatings allow functional versatility in that additional agent(s) can be incorporated to further control the process of preservation of the perishable items or for other purposes. Yet further, certain characteristics (e.g., brittleness) of such coatings maybe modulated without requiring additives, thereby providing tunability, depending on its application.

Biopolymer-based food coatings have been extensively studied and widely employed in the food industry. Perhaps the most common example is the use of wax to coat fruits and vegetables. Waxes are organic compounds that characteristically consist of long alkyl chains. Natural waxes are typically esters of fatty acids and long chain alcohols. Synthetic waxes are long-chain hydrocarbons lacking functional groups. The hydrophobicity of wax makes it an attractive moisture barrier for keeping fruits and vegetables fresh. Wax suitable for food coating is, however, also brittle and is typically used in conjunction with a plasticizing agent (i.e., plasticizer). For instance, wax may be mixed with a biopolymer (e.g., chitosan, gelatin) that acts as a plasticizer.

Other biopolymers that have been employed as coating materials include, but are not limited to, various proteins, such as collagen, gelatin, corn zein, wheat gluten, casein and whey. Both collagen and gelatin are very hydrophilic and therefore, do not provide an effective moisture barrier. Corn zein, on the other hand, is a highly hydrophobic protein and due also to its abundance has been exploited in the food industry for a number of applications. However, as a coating material, because of its brittleness, it typically requires the use of added plasticizer. In addition, zein proteins do not remain transparent in that they turn white upon contact with water (e.g., moisture), which in some applications is not desirable. Wheat gluten also requires a plasticizer to be used as coating materials. Casein and whey may also be used for the production of edible film materials, but generally these are used as composite films. Moreover, addition of plasticizing agents is typically required.

In contrast to these biopolymer-based coatings commercially exploited to date, biopolymer-based coatings described herein provide superior material features with desirable functional attributes. For example, such coating (i) may be used to form a barrier between a perishable item and its environment; (ii) may be used as a carrier for an agent; (iii) may be used as an enhancer of at least one property of the perishable item, or any combination thereof. In any one of these functional parameters, the biopolymer-based coatings described herein exhibit superior performance as compared to commercially available coatings described in prior art.

Coated Perishable Products

Accordingly, in one aspect, products that comprise a perishable item and a coating are provided. Such products include at least one perishable item, at least part of which is in contact with a biopolymer-based coating material.

In the context of the present disclosure, "perishable" products refer to items that are susceptible to at least one type of damage (e.g., reduced quality), which typically involves changes in one or more parameters, such as water content, color, general appearance, taste or flavor, texture (e.g., visual texture such as smoothness and structural texture such as crispness), structural integrity, smell, bacterial or fungal growth, etc. Non-limiting examples of perishable items may include but are not limited to: food items, such as fresh produce (e.g., fruits and vegetables), meat products (e.g., processed meat and raw meat products), grains, nuts, seeds, spores, dairy products (e.g., cheese), beverages (e.g., spirits, wine, juices), processed food (e.g., snacks), tablets and capsules, such as gel-caps, plants and flowers, and the like.

As described in further detail herein, in some embodiments of the invention, coatings used for a perishable item comprise a biopolymer. In some embodiments, coatings described herein are made of protein-based coating materials. The terms "protein" and "polypeptide" are used interchangeably herein unless otherwise specified.

In some embodiments, biopolymer-based coating materials contain one or more proteins. Such materials may further contain additional biopolymer components. For instance, biopolymer-based coating materials of the present invention include those with a second biopolymer (i.e., co-polymer) mixed therein. Additional components may include, without limitation, polypeptides, fatty acids, waxes, starches, carbohydrates and polysaccharides, to name a few. In some embodiments of the invention, a biopolymer-based coating encompassed by the present invention consists essentially of a protein and water.

Structural Characteristics of Preferred Polypeptides

While various protein-based food coatings have been explored to date, the present invention encompasses the recognition that peptides having certain structural features are especially useful as a coating material in accordance with the methods provided herein. In particular, it has been discovered that peptides that overall hydrophobic but are also of amphiphilic in nature are suitable as coating perishable products.

The term "amphiphilic" refers to having both hydrophobic and hydrophilic properties. For example, surfactants and zwitterions are common amphiphilic substances. Typically, an amphiphilic protein contains one or more hydrophobic portions (e.g., stretches, domains, or fractions), as well as one or more hydrophilic portions (e.g., stretches, domains, or fractions), rendering the protein amphiphilic. In some embodiments, amphiphilic peptides can form micellar structures (i.e., micelles) in a solution.

Accordingly, in some embodiments, an amphiphilic polypeptide suitable for the present invention contains one or more hydrophobic portions and one or more hydrophilic portions. In some embodiments, an amphiphilic polypeptide suitable for the present invention contains intervening hydrophobic and hydrophilic segments. In some embodiments, an amphiphilic polypeptide suitable for the present invention contains hydrophobic and hydrophilic segments organized in tandem. In particularly useful embodiments, the hydrophobic segments of an amphiphilic polypeptide are predominant over the hydrophilic segments. For example, in some embodiments, large hydrophobic segments of an amphiphilic polypeptide are linked by shorter segments of hydrophilic linker motifs.

In some embodiments, amphiphilic polypeptides suitable for the present invention comprises a hydrophobic portion that is capable of forming a beta-sheet (β-sheet) secondary structure (e.g., crystalline). In some embodiments, amphiphilic polypeptides suitable for the present invention comprises a plurality of hydrophobic portions that is capable of forming a beta-sheet (β-sheet) secondary structure. In some embodiments, amphiphilic polypeptides suitable for the present invention comprises a hydrophilic portion that is amorphous (e.g., a random coil). In some embodiments, amphiphilic polypeptides suitable for the present invention comprises a plurality of hydrophilic portions that forms a random coil. In some embodiments, amphiphilic polypeptides suitable for the present invention comprises a plurality of hydrophobic portions capable of forming a beta-sheet (β-sheet) secondary structure and a plurality of hydrophilic portions capable of forming a random coil. In some embodiments, the plurality of hydrophobic portions callable of forming a beta-sheet secondary structure and the plurality of hydrophilic portions capable of forming random coil are organized in tandem.

It has been further discovered that amphiphilic peptides that have relatively high overall hydrophobicity are suitable for carrying out the invention described herein. Defining hydrophobicity of proteins on a structural basis is complex since it may be modulated not only by the primary structure (i.e., amino acid sequence), but also involves the secondary and tertiary structures. In the context of the present disclosure, however, amphiphilic peptides suitable for carrying out the described invention typically possess a net hydrophobicity of at least 65% at the amino acid level, e.g., at least 70%, at least 75%, at least 80%, at least 85%, at least 90%, at least 95%, or greater. Thus, as used herein, "net hydrophobicity" of a peptide or protein is determined by dividing the number of hydrophobic amino acids present in the primary sequence by the total number of amino acids, multiplied by 100, expressed as percentage (%).

Among the 20 most commonly occurring amino acids, the following are considered to be "hydrophobic" amino acids; Alanine (Ala/A), Isoleucine (Ile/I), Leucine (Leu/L), Phenylalanine (Phe/F), Valine (Val/V), Proline (Pro/P), Glycine (Gly/G). On the other hand, polar or charged amino acids have higher propensity to be in contact with water (i.e., "hydrophilic") or in other words energetically favorable to be in contact with water. Among the 20 most commonly occurring amino acids, "charged" amino acid residues include Arginine (Arg/R), Lysine (Lys/K), Aspartic acid (Asp/D) and Glutamic acid (Glu/E). Among the 20 most commonly occurring amino acids, "polar" amino acid residues include Glutamine (Gln/Q), Asparagine (Asn/N), Histidine (His/H), Serine (Ser/S), Threonine (Thr/T), Tyrosine (Tyr/Y), Cysteine (Cys/C), Methionine (Met/M) and Tryptophan (Trp/W).

Accordingly, in some embodiments, amphiphilic polypeptides useful for the present invention contain at least 65% of amino acid residues that make up hydrophobic portion(s) (e.g., hydrophobic secondary structures) of the peptide, e.g., at least 65%, at least 70%, at least 75%, at least 80%, at least 85%, at least 90%, at least 95%, or greater. In some embodiments, an amphiphilic polypeptide suitable for the present invention contains at least 65% of its amino acid residues that participate in forming beta-sheet secondary structure(s), e.g., at least 65%, at least 70%, at least 75%, at least 80%, at least 85%, at least 90%, at least 95%, or greater.

Moreover, the inventors of the present application have recognized that the hydrophilic portion or portions of an amphiphilic polypeptide described herein surprisingly may function as a "built-in plasticizer" when used as a coating material. As such, coatings made from such amphiphilic polypeptides do not require an added plasticizing agent.

Accordingly, in some embodiments, amphiphilic polypeptides useful for the present invention contain up to 35% of amino acid residues that make up hydrophilic portion(s) of the peptide, e.g., 35% or less, 30% or less, 25% or less, 20% or less, 15% or less, 10% or less, and 5% or less. In some embodiments, an amphiphilic polypeptide suitable for the present invention contains up to 35% of its amino acid residues that form random coil structure(s), e.g., 35% or less, 30% or less, 25% or less, 20% or less, 15% or less, 10% or less, and 5% or less.

Yet further, it has been recognized by the inventors of the present disclosure that interplay at the molecular level between the hydrophobic (e.g., crystalline) domains and the hydrophilic (e.g., amorphous) domains of a coating protein determines the balance of malleability of the resulting coating. That is, crystalline formation primarily depends on the intra- and inter-molecular interactions of hydrophobic domains via hydrogen bonds as well as hydrophobic interactions, while the structural flexibility or malleability of the coating requires the plasticizing effect rendered by the amorphous domains of such proteins.

This also means that, relative molecular weights or ranges of molecular weights of such peptides that make up a coating have an affect on crystalline formation, or "packing," as well as its stability and structural flexibility, because polypeptides with relatively larger hydrophobic fractions may provide greater molecular interactions (e.g., more hydrogen bonds, etc.) to stabilize the protein structure. Accordingly, in some embodiments of the invention, proteins used for a coating material has an average molecular weight of at least 50 kilo-dalton (kDa). In some embodiments, proteins used for a coating material in accordance with the invention have average molecular weights ranging between about 50 kDa and about 400 kDa. In some embodiments, a protein used for a coating material in accordance with the invention has an average molecular weight of about 50 kDa, about 60 kDa, about 70 kDa, about 80 kDa, about 90 kDa, about 100 kDa, about 110 kDa, about 120 kDa, about 130 kDa, about 140 kDa, about 150 kDa, about 160 kDa, about 170 kDa, about 180 kDa, about 190 kDa, about 200 kDa, about 210 kDa, about 220 kDa, about 230 kDa, about 240 kDa, about 250 kDa, about 260 kDa, about 270 kDa, about 280 kDa, about 290 kDa, about 300 kDa, about 310 kDa, about 320 kDa, about 330 kDa, about 340 kDa, about 350 kDa, about 360 kDa, about 370 kDa, about 380 kDa, about 390 kDa, about 400 kDa, and greater. Typically, such polypeptides are able to form flexible, less brittle coatings without requiring added plasticizing agents.

To give but one example, silk fibroin is a hydrophobic structural protein having amphiphilic properties. Silk fibroin heavy chain are made of amorphous and crystalline fractions. It has been observed that the beta-sheets of fibroin proteins stack to form crystals, whereas the other segments form amorphous domains. It is the interplay between the hard crystalline segments, and the strained elastic semi amorphous regions, that at least in part gives silk its extraordinary properties.

In addition, the protein secondary as well as tertiary structures can be further controlled due to the polymorphism of the protein. This modulation of silk structure allows for a fine control over the protein physical and mechanical properties that result in a flexible and more plastic material, as compared to purely crystalline proteins, such as corn zein. In addition, the molecular weight of regenerated silk fibroin (e.g., from about 390 to about 50 KDa, depending on the processing conditions, such as boiling time) is much higher than the one of regenerated zein (around 15-40 kDa). Without wishing to be bound by a particular theory, it is believed that at such low molecular weight, the intermolecular bonds and the chain entanglement are limited and result in a more brittle material, which indeed requires a plasticizer to make a flexible, conformable film coating. For the same reason, flexible film coatings cannot be typically made using silk fibroin boiled for an extended duration of time (such as 100 min). Such processing causes fragmentations of the protein, and as the molecular weight of the protein becomes too low and the resulting material becomes too brittle.

However, coatings that are brittle may be preferred in certain situations. For example, some perishable products may be desirable to retain crispness. The invention thus includes the use of selected low molecular weight proteins for the preparation of coatings. In some embodiments, low molecular weight proteins have average molecular weight ranging between about 10 kDa and about 45 kDa, e.g., about 10 kDa, about 15 kDa, about 20 kDa, about 25 kDa, about 30 kDa, about 35 kDa, about 40 kDa and about 45 kDa.

A number of amphiphilic polypeptides may be considered for carrying out the present invention. In some embodiments, a polypeptide from a single source (e.g., naturally occurring proteins) may be used, which contains both a hydrophobic module or stretch and a hydrophilic module or stretch within the polypeptide, such that the single polypeptide itself is naturally amphiphilic. In some embodiments, a hydrophobic module or stretch and a hydrophilic module or stretch may be fused or coupled together to form an amphiphilic entity. Such "fusion" or "chimeric" polypeptides may be produced using recombinant techniques, chemical coupling, or both.

Yet further, the present invention encompasses the recognition that polypeptides that include a portion or portions of an amino acid sequence that adopt the beta-sheet (β-sheet) secondary structure are particularly useful for the present invention. Accordingly, in some embodiments, amphiphilic polypeptides are selected on the basis of having a beta-sheet structure or propensity for forming such a structure based on the amino acid sequence.

In some embodiments, peptide-based coatings described herein comprise an amino acid sequence of polypeptides selected from the following list: fibroins, actins, collagens, catenins, claudins, coilins, elastins, elaunins, extensins, fibrillins, lamins, laminins, keratins, tublins, viral structural proteins, zein proteins (seed storage protein) and any combinations thereof. In some embodiments, silk fibroin is used to carry out the present invention. In any of the embodiments, coatings described herein may comprise a silk fibroin polypeptide. In some embodiments, such coatings may be prepared from an aqueous solution that consists essentially of a silk fibroin polypeptide and water.

Amphiphilic polypeptides suitable for practicing the present invention may be produced from various sources, including a regenerated (e.g., purified) protein from natural sources, recombinant proteins produced in heterologous systems, synthetic or chemically produced peptides, or combination of these.

In some embodiments, coatings of the present invention may be prepared from a polypeptide corresponding to any one of the list provided above, with or without one or more amino acid sequence variations, as compared to the native or wild type counterpart. For example, in some embodiments, such variants may show at least 85% overall sequence identity as compared to the wild type sequence, e.g., at least 86%, 87%, 88%, 89%, 90%, 91%, 92%, 93%, 94%, 95%, 96%, 97%, 98%, 99% overall sequence identity. In some embodiments, for example, a coating is prepared using silk fibroin in accordance with the present disclosure. In any of the embodiments, coatings described herein may comprise a silk fibroin polypeptide. In some embodiments, such coatings may consist essentially of a silk fibroin polypeptide and residual water.

Silk Fibroin

As used herein, the term "silk fibroin" refers to silk fibroin protein or fragment thereof, whether produced by silkworm, spider, or other insect, or otherwise generated (Lucas et al., Adv. Protein Chem., 13: 107-242 (1958)). Silk is naturally produced by various species, including, without limitation: *Antheraea mylitta; Antheraea pernyi; Antheraea yamamai; Galleria mellonella; Bombyx mori; Bombyx mardarina; Galleria mellonella; Nephila clavipes; Nephila senegalensis; Gasteracantha mammosa; Argiope aurantia; Araneus diadematus; Latrodectus geometricus; Araneus bicentenarius; Tetragnatha versicolor; Araneus ventricosus; Dolomedes tenebrosus; Euagrus chisoseus; Plectreurys tristis; Argiope trifasciata*; and *Nephila madagascariensis.*

In some embodiments, silk fibroin is obtained from a solution containing a dissolved silkworm silk or spider silk. For example, in some embodiments, silkworm silk fibroins are obtained, from the cocoon of *Bombyx mori*. In some embodiments, spider silk fibroins are obtained, for example, from *Nephila clavipes*. In the alternative, in some embodiments, silk fibroins suitable for use in the invention are obtained from a solution containing a genetically engineered silk or recombinantly produced silk harvested from bacteria, yeast, mammalian cells, transgenic animals or transgenic plants. See, e.g., WO 97/08315 and U.S. Pat. No. 5,245,012, each of which is incorporated herein by reference in its entirety.

Thus, in some embodiments, a silk solution is used to produce coatings of the present invention contain fibroin proteins, essentially free of sericins. "Substantially free" as used herein means that it is absent or present at a concentration that is either (i) below detection measured by any art-accepted means; or, (ii) has no or little impact on downstream application, such that it is considered negligible.

In some embodiments, silk solutions used to fabricate various compositions of the present invention contain the heavy chain of fibroin, but are essentially free of other proteins. In other embodiments, silk solutions used to fabricate various compositions of the present invention contain both the heavy and light chains of fibroin, but are essentially free of other proteins. In certain embodiments, silk solutions used to fabricate various compositions of the present invention comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds.

Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Ala-rich" and "Gly-rich" hydrophobic blocks are typically separated by segments of amino acids with bulky side-groups (e.g., hydrophilic spacers).

In some embodiments, core repeat sequences of the hydrophobic blocks of fibroin are represented by the following amino acid sequences and/or formulae: $(GAGAGS)_{5-15}$ (SEQ ID NO: 1); $(GX)_{5-15}$ (X=V, I, A) (SEQ ID NO: 2); GAAS (SEQ ID NO: 3); (S1-2A11-13) (SEQ ID NO: 4); GX1-4 GGX (SEQ ID NO: 5); GGGX (X=A, S, Y, R, D V, W, R, D) (SEQ ID NO: 6); $(S1-2A1-4)_{1-2}$ (SEQ ID NO: 7); GLGGLG (SEQ ID NO: 8); GXGGXG (X=L, I, V, P) (SEQ ID NO: 9); GPX (X=L, Y, I) (SEQ ID NO:23); $(GP(GGX)_{1-4}Y)n$ (X=Y, V, S, A) (SEQ ID NO: 10); GRGGAn (SEQ ID NO: 11); GGXn (X=A, T, V, S) (SEQ ID NO:24); GAG(A)$_{6-7}$GGA (SEQ ID NO: 12); and GGX GX GXX (X=Q, Y, L, A, S, R) (SEQ ID NO: 13).

In some embodiments, a fibroin peptide contains multiple hydrophobic blocks, e.g., 3, 4, 5, 6, 7, 8, 9, 10, 11, 12, 13, 14, 15, 16, 17, 18, 19 and 20 hydrophobic blocks within the peptide. In some embodiments, a fibroin peptide contains between 4-17 hydrophobic blocks.

In some embodiments of the invention, a fibroin peptide comprises at least one hydrophilic spacer sequence ("hydrophilic block") that is about 4-50 amino acids in length. Non-limiting examples of the hydrophilic spacer sequences include: TGSSGFGPYVNGGYSG (SEQ ID NO: 14); YEYAWSSE (SEQ ID NO: 15); SDFGTGS (SEQ ID NO: 16); RRAGYDR (SEQ ID NO: 17); EVIVIDDR (SEQ ID NO: 18); TTIIEDLDITITIDGADGPI (SEQ ID NO: 19) and TISEELTI (SEQ ID NO: 20).

In certain embodiments, a fibroin peptide contains a hydrophilic spacer sequence that is a derivative of any one of the representative spacer sequences listed above. Such derivatives are at least 75%, at least 80%, at least 85%, at least 90%, or at least 95% identical to any one of the hydrophilic spacer sequences.

As noted, silks are fibrous proteins and are characterized by modular units linked together to form high molecular weight, highly repetitive proteins. These modular units or domains, each with specific amino acid sequences and chemistries, are thought to provide specific functions. For example, sequence motifs such as poly-alanine (polyA) and poly-alanine-glycine (poly-AG) are inclined to be beta-sheet-forming; GXX motifs contribute to 31-helix formation; GXG motifs provide stiffness; and, GPGXX (SEQ ID NO: 22) contributes to beta-spiral formation. These are examples of key components in various silk structures whose positioning and arrangement are intimately tied with the end material properties of silk-based materials (reviewed in Omenetto and Kaplan (2010) Science 329: 528-531). Also see: WO 2011/130335 (PCT/US2011/032195), the contents of which are incorporated herein by reference.

In any of the embodiments contemplated herein, silk fibroin polypeptides of various molecular weights (e.g., fragments) may be used. In some embodiments, for example, provided silk fibroin coatings comprise silk fibroin polypeptides having an average molecular weight of between about 3.5 kDa and about 350 kDa. Non-limiting examples of suitable ranges of silk fibroin fragments include, but are not limited to: silk fibroin polypeptides having an average molecular weight of between about 50 kDa and about 350 kDa; silk fibroin polypeptides having an average molecular weight of between about 100 kDa and about 350 kDa; silk fibroin polypeptides having an average molecular weight of between about 150 and about 350 kDa; silk fibroin polypeptides having an average molecular weight of between about 200 kDa and about 350 kDa, and so on. Silk fibroin polypeptides that are "reduced" in size, for instance, smaller than the original or wild type counterpart, may be referred to as "low molecular weight silk fibroin."

Optional Additives—Plasticizers

In any of the embodiments embraced by the present invention, biopolymer-based coatings may further include one or more additives. While not required, examples of suitable additives may include, without limitation, one or more plasticizing agents (i.e., plasticizers) and other active or inactive agents, depending on particular use.

As used in the context of the present disclosure, the terms "plasticizing agent" and "plasticizer" are used interchangeably herein and are understood to mean any substance added to a biopolymer-based coating preparation to promote plasticity and flexibility and to reduce brittleness. Typically, such an agent is a hygroscopic substance that forms hydrogen or electrostatic bonds with the biopolymer and that increases the amount of free and freezing bond water retained in the biopolymer materials. One example of such an agent is glycerol. It should be noted, however, that at least some plasticizers commonly used for conventional preparations (e.g., certain oils) may not work with biopolymer-based coatings described in the present application. In some embodiments, biopolymer-based coatings include one or more plasticizing agents, including, but are not limited to: Glycerin; Glyceryl oleate; Oleyl alcohol; PEG-4 PEG-6; PEG-8; PEG-12; PEG-16; PEG-20 PEG-32; PEG-75 (Ref. Handbook of Green Chemistry, Part IV Functional/Application, pp. 2759), stearic acid, oleic acid, sodium lactate, Emerest® 2618; Emerest® 2619; Hydrobrite® 200PO; Hydrobrite® 380PO; Hydrobrite® 550PO PEG-20 stearate; Propylene glycol laurate; Semtol® 40; Semtol® 70; Semtol® 85 Semtol® 100; Semtol® 350 (Ref. Handbook of Green Chemistry, Part IV Functional/Application, pp, 2755).

In some embodiments, biopolymer-based coating preparations may further comprise one or more humectants. Generally, a humectant is a water soluble solvent and any one of a group of hygroscopic substances with hydrating properties, i.e., used to keep things moist. They often are a molecule with several hydrophilic groups, most often hydroxyl groups; however, amines and carboxyl groups, sometimes esterified, can be encountered as well (its affinity to form hydrogen bonds with molecules of water, is the crucial trait).

Non-limiting examples of some humectants include: propylene glycol (E1520), hexylene glycol, and butylene glycol; glyceryl triacetate (E1518); vinyl alcohol; neoagarobiose; Sugar alcohols/sugar polyols: glycerol/glycerin, sorbitol (E420), xylitol, maltitol (E965); polymeric polyols (e.g., polydextrose (E1200)); quillaia (E999); urea; aloe vera gel; MP Diol; alpha hydroxy acids (e.g., lactic acid); and, honey.

Optional Additives—Other Components

According to the present invention, biopolymer-based coatings may further include one or more additional components of interest. Such components may be active agents or inactive (or inert) agents. Non-limiting examples of additives that may be incorporated into the coating materials include biologically active agents such as: anti-microbe agents, such as antibacterial agents and antifungal agents; enzyme inhibitors; ethylene-capturing/binding molecules, such as ethylene-binding domains of ethylene receptors; ethylene-absorbing substances, such as aluminosilicates (e.g., zeolites), silk fibroin-based aerogels (See, U.S. Provisional Application 61/902,145 filed Nov. 8, 2013, entitled "PEPTIDE-BASED NANOFIBRILLAR MATERIALS" which is incorporated herein) oxidizing agents, such as potassium permanganate; ethylene receptor antagonists; porphyrins; hormones, hormone receptor agonists and antagonists thereof.

Other additives that may be incorporated into the coating materials include, but are not limited to: nutraceutical agents (dietary supplements such as: vitamins, antioxidants, fatty acids, etc.); flavorings and other compounds added to improve taste, such as sugars; perfumes or fragrances, colorings, dyes, and so on.

Functional Characteristics

As demonstrated in the exemplification provided below, biopolymer-based coatings described in the present application exhibit low water permeability and therefore are capable of forming an effective moisture barrier to prevent the loss of moisture from perishable products. This is important for both keeping moisture inside perishable products with relatively high water contents, such as fresh fruits, by preventing dehydration, as well as keeping moisture out to maintain dry products. Controlling water permeability may also help control microbe growth and contamination.

In some embodiments, biopolymer-based coatings described in the present application have a water diffusivity of less than $10^{-6}$ cm$^2$/s, e.g., less than $10^{-7}$ cm$^2$/s, less than $10^{-8}$ cm$^2$/s, less than $10^{-9}$ cm$^2$/s, or less. In some embodiments, such coatings have a water diffusivity ranging between about $10^{-6}$ cm$^2$/s and about $10^{-9}$ cm$^2$/s, e.g., between about $10^{-7}$ cm$^2$/s and about $10^{-7}$ cm$^2$/s, between about $10^{-6}$ cm$^2$/s and about $10^{-8}$ cm$^2$/s, between about $10^{-7}$ cm$^2$/s and about $10^{-8}$ cm$^2$/s, between about $10^{-7}$ cm$^2$/s and about $10^{-9}$ cm$^2$/s, and between about $10^{-8}$ cm$^2$/s and about $10^{-9}$ cm$^2$/s.

In some embodiments, biopolymer-based coatings described in the present application exhibit low gas permeability. In some embodiments, coatings described herein have an oxygen permeability coefficient ($Dk_{O_2}$) of less than $10^{-16}$ [(ml$_{O_2}$·cm)/(cm·s·mmHg)]. In some embodiments, such coatings have an oxygen permeability coefficient ($Dk_{O_2}$) ranging between about $10^{-10}$ and about $10^{-13}$ [(ml$_{O_2}$·cm)/(cm·s·mmHg)], e.g., between about $10^{-10}$ and about $10^{-12}$ [(ml$_{O_2}$·cm)/(cm·s·mmHg)], between about $10^{-10}$ and about $10^{-11}$ [(ml$_{O_2}$·cm)/(cm·s·mmHg)], between about $10^{-11}$ and about $10^{-13}$ [(ml$_{O_2}$·cm)/(cm·s·mmHg)], between about $10^{-11}$ and about $10^{-12}$ [(ml$_{O_2}$·cm)/(cm·s·mmHg)]. In some embodiments, an oxygen permeability coefficient ($Dk_{O_2}$) of described coatings is about $10^{-13}$ [(ml$_{O_2}$·cm)/(cm·s·mmHg)], about $10^{-12}$ [(ml$_{O_2}$·cm)/(cm·s·mmHg)], or about $10^{-11}$ [(ml$_{O_2}$·cm)/(cm·s·mmHg)], about $10^{-10}$ [(ml$_{O_2}$·cm)/(cm·s·mmHg)].

In some embodiments of the invention, biopolymer-based coatings described in the present application are useful for the enhanced or improved ability to preserve perishable items that are susceptible to dehydration, susceptible to discoloration, susceptible to oxidation, susceptible to photodegradation, susceptible to enzymatic degradation, susceptible to decay caused by microbe, ethylene-sensitive, emit ethylene, susceptible to mechanical bruising, or any combination thereof.

In some embodiments biopolymer-based coatings made from an amphiphilic, but hydrophobic polypeptide are used to preserve fresh produce. In some embodiments, perishable products such as fruits are coaled one or more times with a biopolymer coating.

Thus, the invention provides methods for enhanced preservation of perishable items that are susceptible to decay or fermentation caused by fungus (e.g., mold), bacteria, or combination thereof. Generally, freshness of perishable products is better-preserved when such products are coated multiple times with the biopolymer-based coating described herein, and also when the protein crystalline formation is induced in the coating material, resulting in prolonged preservation observed by structural integrity and appearance of external and internal tissues of the products following standard storage. Correspondingly, increasing coating steps and increasing protein crystallinity resulted in the down-regulation of microbial growth, visible by reduced fungal and mold decay.

In some embodiments, suitable storage conditions involve storing a perishable item at a temperature ranging between about 2° C. and about 50° C., but more typically between about 2° C. and about 35° C., e.g., about 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., etc.

In any of such embodiments, suitable storage conditions involve storing a perishable item under certain humidity levels, e.g., less than 5%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%.

In any of such embodiments, suitable storage conditions involve storing a perishable item for a duration of time, ranging between about 1 hour and about 3 years. More typically, storage duration ranges between about 1 day and about 1 year, e.g., about 1 day, 2 days, 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 month, 12 months, or longer.

Coatings prepared and used in accordance with the present application may significantly extend the shelf-life of perishable products coated or packaged therewith. "Shelf-life" is generally defined as the duration of time that a commodity may be stored without becoming unfit for use or consumption. Thus, shelf-life is the recommended maximum time, for which products can be stored, during which the defined quality of a specified proportion of the goods remains acceptable under expected (or specified) conditions of distribution, storage and display.

In some regions, an advisory best before, mandatory use by or freshness date is required on packaged perishable foods. Coatings described herein may include such information.

Generally, "expiry dates" are used as guidelines based on normal and expected handling and exposure to temperature. Use prior to the expiration date does not guarantee the safety of a perishable product, and such a product is not necessarily dangerous or ineffective after the expiration date.

For food items, shelf-life is typically different from expiration date in that the former refers to food quality, while the latter refers to food safety. A perishable product that has passed its shelf life might still be safe, but quality is no longer guaranteed.

In some embodiments, use of a coating described herein prolongs the shelf-life of a perishable product coated therewith, as compared to the same or similar product without the described coating, when both products are processed and stored otherwise under identical or substantially identical conditions. With the use of the described coating, in some embodiments, the shelf-life of a perishable product is extended by at least 5%, at least 10%, at least 15%, at least 20%, at least 25%, at least 30%, at least 35%, at least 40%, at least 45%, at least 50%, at least 55%, at least 60%, at least 70%, at least 75%, at least 80%, at least 85%, at least 90%, at least 95%, or greater, relative to the shelf-life of an equivalent product under the otherwise same processing and storage conditions, with the exception of the coating.

In some embodiments, an average shelf-life of a perishable item coaled with a coating described in the present application is increased by between about 1.1 and about 10 fold, as compared to the corresponding counterpart (e.g., reference), i.e., an item without the inventive coating, e.g., about 1.2 about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.5, about 5.0, about 5.5, about 6.0, about 6.5, about 7.0, about 7.5, about 8.0, about 8.5, about 9.0, about 9.5, and about 10 fold.

In some embodiments, an average shelf-life of a perishable product coated with a coating described herein, as compared to a reference product without such coating, is extended by at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 5 weeks, at least 6 weeks, at least 7 weeks, at least 8 weeks, at least 9 weeks, at least 10 weeks, at least 11 weeks, at least 12 weeks, at least 4 months, at least 5 months, at least 6 months, at least 7 months, at least 8 months, at least 9 months, at least 10 months, at least 11 months, at least 1 year, at least 18 months, at least 2 years, at least 30 months, at least 3 years, at least 4 years, at least 5 years, or longer.

In some embodiments, coatings described in the present disclosure can reduce the need for, or even eliminate, the conventional cold chain requirement typically employed for a particular perishable product. For example, in some embodiments, perishable products that are typically shipped and/or stored at certain ranges of preferred or recommended temperatures may retain one or more parameters of product quality outside such temperature ranges, when coated with a coating described according to the present invention. In some embodiments, products coated with such a coating may withstand a greater degree of deviations and/or fluctuations in temperature, moisture, mechanical stress, light exposure, or any combination thereof, as determined by any one of parameters described herein or other suitable methods known in the art.

Measurements of Preservation

There are a number of parameters to measure relative efficacy of food preservation. Any suitable means may be employed to measure or assay for the degree of freshness or preservation of, or assess the quality of, perishable products before and after or over the course of storage. These include, without limitation, changes in weight, which may reflect water loss, changes in shape or overall structural integrity, changes in texture such as firmness, changes in colors including overall shading or local spotting, changes in chemical species (e.g., contents of sugar, starch, etc.), changes in acidity, changes in smell, taste, etc. Relative gas exchange rates (e.g., oxygen permeability) may also be measured. In addition, emission of specific compounds such as ethylene may be measured. Non-limiting examples of selected measurements are provided in the Exemplification below.

Climacteric Fruits and Non-Climacteric Fruits

Fruits that ripen through ethylene production and increased cell respiration are called climacteric. Examples of climacteric fruits include, without limitation, apples, bananas, and tomatoes. By contrast, berries and grapes are non-climacteric fruits. The climacteric event is said to be associated with changes in fruit color and with the production of sugar in the extracellular space.

As shown in the working examples provided in the present disclosure, biopolymer-based coatings described herein are effective in preserving both climacteric and non-climacteric types of produce. In some embodiments, biopolymer-based coatings described herein may be used to retard the rate of ripening process of fruits. In some embodiments, biopolymer-based coatings described herein may be used to maintain the firmness of fruits. In some embodiments, biopolymer-based coatings described herein may be used to slow microbe growth. In some embodiments, certain fruits, such as non-climacteric fruits (e.g., berries), coated with a biopolymer-based coating described herein, may show very limited presence of "black spots" which are typically indicative of the presence of mold on the surface of the fruits.

In some embodiments, protein polymorphism may be used to tailor the properties of the coating, affecting the interplay between the protein (such as silk fibroin) and water evaporation and the microbial-driven food decay.

General Methods and Applications

In further aspect, related methods for preserving perishable products are provided.

In a broad sense, such method involves adding a coating to at least part of a perishable item desired to be stored or preserved. Typically, at least a portion of the perishable item is in direct contact with at least a portion of a coating comprising a biopolymer as described in more detail above.

A perishable item is said to be preserved, at least in part, when it retains one or more properties or the original status/features, as measured by any suitable parameters, such as water content, color, weight, shape, texture, structural integrity, taste, flavor, smell, and so on.

A biopolymer coating described herein is prepared as an aqueous solution of a suitable biopolymer, e.g., amphiphilic polypeptides having overall hydrophobic characteristics, as described above. Typically, coating materials are prepared as a solution with the biopolymer dissolved therein, at a final concentration of about 0.1-20% by weight, e.g., about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, or greater.

If desired, certain additives may be added into such solutions.

Any suitable techniques may be used to perform the step of coating (e.g., step of depositing a coating material onto a perishable item). For example, the coating process may be carried out by any suitable means, including but are not limited to, dip-coating, spray-coating, brushing on, and so on. Such step may be carried out once or repeated multiple times, e.g., 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, 25 times 26 times, 27 times, 28 times, 29 times, 30 times, or more.

Between or following each or one of the coating steps, the biopolymer-based coating may be dried, and optionally annealed, crossed-linked, or both. Data presented in the present disclosure suggest that increasing the degree of crystallinity in the biopolymer may enhance the preserving effects. These effects may involve at least two factors: one is the prevention of water loss, and the other is the prevention of microbe growth.

In some embodiments, the process of annealing may involve inducing beta-sheet formation in the biopolymer used as a coating material. Techniques of annealing (e.g., increase crystallinity) or otherwise promoting "molecular packing" of biopolymers have been described.

In some embodiments, annealing (e.g., the beta sheet formation) is induced by addition of an organic solvent. Suitable organic solvents include, but are not limited to: methanol, ethanol, acetone, isopropanol, or combination thereof.

In some embodiments, annealing is carried out by so-called "water-annealing" or "water vapor annealing" in which water vapor is used as an intermediate plasticizing agent or catalyst to promote the packing of beta-sheets. In some embodiments, the process of water annealing may be performed under vacuum. Suitable such methods have been described. See, for example, Jin H-J et al. (2005), Water-stable Silk Films with Reduced Beta-Sheet Content, Advanced Functional Materials, 15: 1241-1247; Xiao H. et al. (2011), Regulation of Silk Material Structure by Temperature-Controlled Water Vapor Annealing, Biomacromolecules, 12(5): 1686-1696.

In some embodiments, the step of annealing or crosslinking involves exposing the amphiphilic polypeptide of the coating material to a high energy source, such as by irradiation.

Useful source of high energy for such a process may include an electron beam, photons, ionizing radiation, nuclear radiation, without limitation.

According to the invention, at least a portion of a perishable item may be coated or covered with a biopolymer-based coating in one or more layers. A layer of such coatings may be of any suitable thickness, for example, between about 0.1 µm and about 1 mm, e.g., about 0.5 µm, about 1 µm, about 5 µm, about 10 µm, about 15 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 900 µm, about 950 µm, about 1000 µm, or greater. Such a coating may be comprised of single layer or multiple layers of coatings.

In some embodiments, biopolymer-based coatings of the present invention form conformal covering or sheath on at least a portion of the surface of a perishable product. In some embodiments, such coatings may completely ensheathe one or all surfaces of a perishable product.

Biopolymer-based coatings of the present invention may be substantially transparent when formed as a coating on a perishable product. Transparency is a desirable feature for keeping the natural color or appearance of the perishable product. Additionally, in some embodiments, such coatings may have an effect of added sheen (e.g., glossy appearance) to the product being coated.

Typically, biopolymer-based coatings described herein are odorless, flavorless, or both.

In some embodiments, biopolymer-based coatings described herein can be made sufficiently water-soluble and therefore are easily washable. However, in some embodiments, coatings on perishable food items do not require removal before consumption.

Biopolymer-based coatings encompassed by the present invention may also be used as packaging materials for a variety of products. For example, biopolymer-based coatings provided herein may at least in part replace any conventional packaging materials that are used to wrap, cover, or bottle perishable items, including, without limitation, dairy products, wines and spirits, other bottled beverages, and the like.

In some embodiments, conventional packaging materials may be coated at least on one side with a biopolymer-based coating described herein. In some embodiments, a component of packaging may be replaced with or incorporate a biopolymer-based coating described herein. For instance, biopolymer-based coating materials may be used as a wine stopper to replace cork.

In any of the embodiment embraced by the present invention, coatings may further comprise one or more additional features, such as nano- and/or micro-structures fabricated thereon or incorporated therein. Such structures may provide at least one optical feature to the coating. Examples of optical features include, but are not limited to: diffractive gratings, nano-scale pits and holes, microprisms, and the like. In some embodiments, such structures are designed to act as sensors. See, for example, WO 2008/127404; WO 2008/118211; WO 2008/127402; WO 2008/127403; WO 2008/127401; WO 2008/140562; WO 2009/061823; WO 2009/155397; WO 2010/126640; WO 2011/046652; WO 2011/026101; WO 2012/054121; WO 2011/130335; WO 2011/112931; WO 2012/047682; WO 2012/031282; WO 2010/088585; WO 2013/130156; contents of each of the above-listed publications are incorporated herein by reference in their entirety.

In some embodiments, such optical and/or nano-scale features are designed to carry or encode certain information (e.g., labels and codes). Any suitable or desirable information may be encoded or included, including, without limitation, identification information, such as information about the source or origin of a product, ingredients, nutritional information, manufacturing information, processing dates (date of harvest, date of coating or packaging, etc.), an advisory best before, mandatory use by, or freshness date, expiry dates, pricing information, authentication, advertisement, customer service information, or any combination thereof.

In any of the embodiments embraced herein, additional feature or features added to coatings of the present invention may provide aesthetic effects, such as designs, patterns, colorings, pictures, images, logos, and any combinations thereof.

The following Exemplification provides non-limiting embodiments of working examples carried out in accordance with the present invention described herein. The data are presented for illustrative purposes only and are not to be construed in any way to be limiting.

EXEMPLIFICATION

Silk Fibroin as Edible Coating for Perishable Food Preservation

Many perishable foods possess high metabolic activity and suffer from high possibility of microbial contamination, resulting in short shell-life, fungal decay, color change, and off-flavor. Among all the perishable food, for example, strawberries are considered one of the most difficult to preserve fresh in the "farm to table" process and are therefore used as a model to test the efficacy of perishable food preservation strategies described in the present disclosure. Strawberries are rich in polyphenols and anthocyanins, vitamins and amino acids. To date, several options have been used to preserve the freshness of strawberries. These include, synthetic chemical fungicides, modified atmosphere packaging, osmotic treatments, hypobaric and heat treatments, cryopreservation and edible coatings. Edible coatings, in particular, have been widely studied in the recent years as their beneficial effects and easy handling made them broadly applicable to soft fruits, such as the berries. In particular, the main functional advantages attributed to the use of edible coatings include slower respiration rate, extended storage periods, firmness retention and controlled microbial growth. Several classes of biopolymers have been contemplated for developing edible coatings: polysaccharides, proteins, lipids, as well as various combinations of these biopolymers. Polysaccharides and proteins are known to form films with good mechanical properties, but with poor permeability, while the lipids form brittle films but with improved permeability. Therefore, research for edible fruit coating is now focused on using robust polymeric matrices with hydrophobic groups to combine mechanical robustness with low permeability to water vapors. In addition, an ideal coating material for perishable food preservation should possess biocompatibility, biodegradability, antibacterial and antifungal activities, membrane forming capacity and safety (i.e. edible and not allergenic).

Silk fibroin is an extensively investigated biomaterial for its potential in textile, biomedical, photonic and electronic applications. Silk fibroin is a structural protein, like collagen, but with a unique feature: it is produced from the extrusion of an amino-acidic solution by a living complex organism (while collagen is produced in the extracellular space by self-assembly of cell-produced monomers). Silk fibroin properties are derived from its structure, which consists of hydrophobic blocks staggered by hydrophilic, acidic spacers. In its natural state, silk fibroin is organized in β-sheet crystals alternated with amorphous regions, which provide strength and resilience to the protein. The multiplicities of forms in which regenerated silk fibroin can be processed into at a high protein concentration and molecular weight make it attractive for several high-tech applications, as recently reported. The degree of crystallinity of the protein can be finely tuned and it influences the material's physical, biochemical, mechanical and biological properties. In addition, the amino-acidic nature of silk fibroin brings a diversity of side chain chemistries that allows for the incorporation and stabilization of macromolecules useful in drug delivery applications or in providing cellular instructions. In particular, silk fibroin with modular degrees of crystallinity can be obtained by regulating the time (minutes to hour range) and temperature (4-60° C.) to which the protein get exposed to water vapor or edible polar solvents (i.e. ethanol). Silk fibroin crystallinity degree stabilizes vaccines and antibiotics, eliminating the need for the cold chain. Silk is indeed considered a platform technology in biomaterials fabrication as its robustness and qualities bring needed assets to provide a portfolio of distinct features (e.g. nanopatterning, biochemical functionalization) for the final construct. Processing of regenerated fibroin generally involves the partial or total dehydration of a fibroin solution (protein content of 1-15 wt %) to form films, sponges, gels, spheres (micron- to nano-sized) and foams with numerous techniques (e.g. solvent casting, freeze drying, salt leaching, or sonication). The rationale beyond these fabrication processes is to manufacture a robust material that combines mechanical strength with biochemical properties.

In this study, we report the use of silk fibroin solution as coating material for perishable fruit preservation. Silk fibroin solution obtained as previously described was used to coat freshly picked strawberries through dip-coating, as shown in FIG. 1 at panel (a). Set D. Rockwood, R. Preda, T. Yucel, X. Wang, M. Lovett, D. Kaplan, Nature Protocols 2011.6, 1612, which is hereby incorporated by reference in its entirety.

Several silk fibroin solutions characterized by changes in molecular weight and protein concentration have been investigated. In addition, the exposure of strawberries to multiple dip-coating steps have been evaluated as well as the post-processing of the coated fruit in water vapor under vacuum (previously described as water-annealing process) have been investigated to explore the effects of the coating polymorphism on the fruit stabilization. The results suggested that silk fibroin prolonged the freshness of perishable fruits by slowing fruit respiration, extending fruit firmness, preventing dehydration and preventing microbial growth.

The molecular weight of silk fibroin was tailored in the 170-90 kDa range by regulating the boiling time (i.e. 30 minutes) during fibroin extraction and the concentration of the protein in the dipping solution was adjusted to 1 wt % to obtained a final solution with rheological properties (i.e. viscosity and surface tension) similar to the one of previously optimized biopolymer-based coating solutions. See C. Ribeiro, A. A. Vicente, J. A. Teixeira, C. Miranda, Postharvest Biology and Technology 2007, 44, 63; A. Matsumoto, A. Lindsay, B. Abedian, D. L. Kaplan. Macromolecular Bioscience 2008, 8, 1006; each of which is hereby incorporated by reference in its entirely. The coating of strawberries with silk fibroin was achieved with a two-phase process. In the first phase, a multiple-step dip coating process (number of coating steps=1, 2 and 4) was used to expose strawberries to silk fibroin solution. Secondly, the silk fibroin coated fruits were exposed to water vapor under vacuum (namely a water annealing post process) to explore the effects of silk fibroin polymorphism on the fruit stabilization. See X. Hu, K. Shmelev, L. Sun, E.-S., Gil, S.-H. Park, P. Cebe, D. L. Kaplan, Biomacromolecules 2011, 12, 1686, which is hereby incorporated by reference in its entirety. The results suggested that silk fibroin prolonged the freshness of perishable fruits by slowing fruit respiration, extending fruit firmness, preventing dehydration and preventing microbial growth.

Materials and Methods
Silk Fibroin Regeneration

Cocoon from *Bombyx mori* were used as source of fibroin. Extraction of silk fibroin was achieved by standard degumming process, which involved boiling (t=50 minutes) 2.5 g of chopped silk cocoons per liter of 0.02 M sodium carbonate solution. Silk fibroin was then solubilized in 9.3 M lithium bromide for 4 hours in a 60° C. oven. The chaotropic salt was subsequently removed through dialysis (3.5 kDa MWCO) against Milli-Q water for a total of 72 hours, yielding an 8% (w/v) silk fibroin solution. The resulting silk fibroin solution was then purified by centrifugation at 9000 rpm (~12,700 g) over two 25 minute-long periods, at a constant of 4° C. The final concentration of silk fibroin solution was then adjusted to 5 wt % by adding MilliQ water.

Strawberry Dip-Coating

Freshly picked New England native strawberries (Dzen Brother Farm, South Windsor, Conn.) were dip coated for 1, 2 and 4 times (namely D1, D2 and D4) in a 60 mm-deep silk fibroin solution (1 wt %) at 4° C. ensuring that the whole surface of the strawberries and of their calyx and epicalyx were exposed to the solution. The dipping step(s) last for 10 seconds each and then strawberries were dried by hanging them from the peduncle for 4 hours at 22° C., 38% RH.

Banana Dip-Coating

Bananas (Del Monte) green in color were bought from a local store (Whole Foods, Medford Mass.) and then dip-coated with silk fibroin as aforementioned.

Coating Crystallization

Silk fibroin coating crystallization was obtained through exposure of coated strawberries to water vapors under vacuum (namely water annealing), according to previously developed protocols. Exposure time was set to 0 seconds, 1 hour, 6 hours, and 12 hours (namely C0, C1, C6, and C12). To longer water annealing post-processing corresponded an increased crystallinity of silk fibroin, as previously reported.

Evaluation of Strawberry Freshness

The effect of different silk fibroin coating and of water-annealing post-processing on strawberry freshness was evaluated morphologically and gravimetrically. Changes in strawberries color, shape, and formation of microbial colonies were evaluated through time-lapse photography. Gravimetric analysis of berries as received in the laboratory, after dip-coating and at days 1, 3, 5 and 7 was evaluated with a standard laboratory balance (Mettler Toledo MS204S). Berries weight was calculated as an average of three measurements.

Interplay Between Water and Thin Silk Membrane

Interactions of silk fibroin thin membranes with water were investigated through the lenses of capillary wicking, hydrodynamic permeability, and diffusive behaviors. Analysis of the wicking behavior of silk films was looked at along both the Z, and XY axes of the films, with and without the aid of gravitational pressure, as well as horizontally. Thin silk membranes were partially exposed to Rhodamine 6G (Rh6G) solution, which served as a colorimetric indicator for the solvent front progress through the silk fibroin membranes. The hydrodynamic permeability of the films was assessed through Darcy's Law like experiments. Silk fibroin membranes were sandwiched between two pieces of acrylic, with a silicone O-ring to prevent leaks, and then clamped on all sides using screws. Syringes glued to the acrylic and scaled with silicone sealant held 4 mL of water above the film, along with a scale, and collected water passing through from below. The sides and top were sealed with parafilm to limit evaporative losses, and a few pinholes were poked in the cylinder below to avoid any (however slight) vacuum from forming. The water reservoir above the film applied a pressure of ~500 Pa driving the water through the membrane. Diffusivity of water in silk membrane was considered in the context of existing theory of mass transport of water in amorphous polymer systems. We considered this assumption valid also in the case of crystalline silk membranes, as silk fibroin crystals possess highly hydrophobic, intermolecularly cross-linked beta-sheeted structures that will confine water diffusion through the amorphous regions of the protein. Therefore, water transport through silk fibroin membranes will fall into the Fickian or in one of the non-Fickian regimes, depending on the relative timescales between water diffusion and stress-relaxation of the polymeric matrix. Peppas et al. have developed a generalized diffusion expression for amorphous polymers:

$$\frac{M_t}{M_\infty} = kt^n \tag{1}$$

where $M_1$ represents the mass of water uptake at time t, $M\infty$ represents the mass of water uptake as time approaches infinity and k and n are fitting parameters. In particular, the value of the exponent n can be utilized to identify the regime of mass transport under the test conditions. Membranes were prepared according to the conditions described above, at an area of 1 cm². Each dry silk fibroin membrane (thickness of about ≅90±20 μm) was left overnight to equilibrate with the surrounding environment (~22° C., ~38% RH), before being weighted. Silk fibroin membranes were then immersed in Milli-Q water for 1 hour to allow re-swelling and re-weighted after removal of water excess through gentle blotting. This was considered $M_{t-0}$. Subsequent measurements were made at one minute intervals over the next hour until the film reached again the equilibrium with the surrounding dry environment, having returned to its original mass. Indeed, $M_1$ was calculated as $M_1$-$M_{t=0}$, and $M_\infty$ was calculated as $M_{t-1h}$-$M_{t-0}$.

Measurement of oxygen diffusion in silk fibroin films.

The effective oxygen diffusion coefficients were measured in silk fibroin films (n=5) of increasing crystallinity (C1, C6, and C12) using a conventional diffusion system—Microx TX3 Microsensor Oxygen Meter (Presens, Germany) equipped with an Oxygen Microptode (Presens, Germany) and a PermeGear sealed, water-jacked, gas chamber, as previously described. See J. E. Valentin, D. O. Freytes, J. M Grasman, C. Pesyna, J. Freund, T. W. Gilbert, S. F. Badylak, Journal of Biomedical Materials Research Part A 2009, 91A, 1010; C. Androjna, J. E. Gatica, J. M. Belovich, K. A. Derwin, Tissue Engineering Part A 2008, 14, 559, the contents of which is hereby incorporated by reference in its entirety. The system consisted of two compartments that contained known (measured) concentrations of oxygen, separated by the silk film of interest. The opening between the two chambers had an area of 2.75 cm². Silk fibroin film thickness was measured with a micrometer (n=7). Before use, a two-point calibration was performed according to manufacturer protocols using an oxygen free environment (sodium sulfite) and an air-saturated environment (water vapor). The average of the initial and final oxygen concentration readings was used for diffusivity data analysis. Oxygen concentrations were measured at 10 minutes intervals and each silk fibroin film was tested 3 times consecutively.

The effective oxygen diffusion coefficient was calculated as previously reported. See J. E. Valentin, D. O. Freytes, J. M. Grasman, C. Pesyna, J. Freund, T. W. Gilbert, S. F. Badylak, Journal of Biomedical Materials Research Part A 2009, 91A, 1010; C. Androjna, J. E. Gatica, J. M. Belovich, K. A. Derwin, Tissue Engineering Part A 2008, 14, 559, the contents of which is hereby incorporated by reference in its entirety, in brief, under the assumptions of (i) well-mixed fluid in the diffusion system, (ii) no oxygen consumption, (iii) linear oxygen concentration across the tested silk films and (iv) instantaneous steady state, the Fick's Law can be applied to derive the following equations:

$$\ln\left(\frac{C_D - C_R}{C_D - C_{R0}}\right) \cdot \left(\frac{1}{-\beta}\right) = D't \quad (2)$$

$$\beta = \frac{A}{z}\left(\frac{1}{V_R}\right)t \quad (3)$$

where the D' is the system diffusion factor (which depends on the effective silk film oxygen diffusion coefficient $D_{e,M}$ and on the baseline volumetric diffusion factor $D_B$), t is time, β is the effective membrane characteristic geometric constant, A is the area through which diffusion occurs, z is the thickness of the test membrane, $V_R$ is the volume of the receiver chamber, $C_D$ is the concentration of dissolved oxygen in the donor chamber, $C_R$ is the concentration of dissolved oxygen in the receiver chamber at time t; and $C_{R0}$ is the concentration of dissolved oxygen in the receiver chamber at t=0 (at t=0, $C_R=C_{R0}$). The baseline volumetric diffusion factor ($D_B$) is determined by replacing silk film samples with an oxygen impermeable barrier (i.e. rubber made stopper). Because it is assumed that in this case $D_{e,M}=0$, then equation (2) becomes:

$$\ln\left(\frac{C_D - C_R}{C_D - C_{R0}}\right) = \frac{D_B}{V_R}t \quad (4)$$

The effective silk film oxygen diffusion coefficient $D_{e,M}$ is then calculated as:

$$D_{e,M} = \frac{1}{\beta}\left(D' - \frac{D_B}{V_R}\right) \quad (5)$$

Measurement of strawberry respiration rate.

A previously published method was followed to measure the respiration rate of strawberries. In brief, strawberry samples (around 100 g, n=3) were placed in 1 L hermetic glass jars with a septum in the lid for sampling gas at different sampling times, over period of 36 hours. The jars were stored at ambient temperature of 22° C. and RH=38%. Gas sampling was carried out every 30 minutes (or the first 5 hours, every 90 minutes till the 12th hour and every 180 minutes for the remaining 24 hours with a needle probe. Three replicates were performed for each coating treatment. The respiration rate was calculated by using the following equation:

$$\text{Respiration rate} = \frac{\Delta CO_2}{100} \cdot V_{headspace} \cdot \frac{1000}{m} \cdot \frac{60}{t} \left[\frac{mlCO_2}{kg \cdot h}\right] \quad (6)$$

where m is mass of strawberry, $V_{headspace}$ is the empty volume of the hermetic jar [ml], $\Delta CO_2$ is the difference between the initial and final concentration of $CO_2$ and t is sampling time [min].

Measurement of strawberry firmness.

The firmness of silk fibroin uncoated and coated strawberries was measured at 22° C. and RH=38% through a puncture test using an Instron uniaxial system equipped with a 10 N load cell. Strawberry firmness was evaluated as a function of storage time (as received, days 1, 3 and 7) and silk fibroin crystallinity degree. The test was performed according to a previously reported protocol. See E. Velickova, E. Winkelhausen, S. Kuzmanova, V. D. Alves, M. Moldão-Martins, LWT—Food Science and Technology 2013, 52, 80, the contents of which are hereby incorporated by reference in their entirety herein. In brief, a 5 mm diameter stainless steel rod with a flat end was used as probe to penetrate the strawberries analyzed. The maximum penetration force (N) was defined as the maximum force required to push the probe into the strawberries (n=5) to a depth of 8 mm at a cross-head speed of 1 mm/s.

Example 1

Results and Discussion

Time-Lapse Photography

Figure 2:
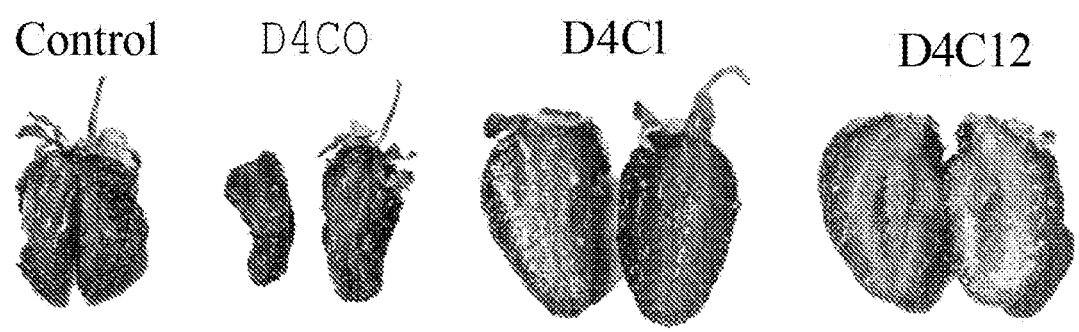
FIG. 2 provides comparative images showing internal tissues of berries after seven days of storage in standard conditions. Berries were stored at 22° C. and 38% RH as received (control) and after coating with silk fibroin solution (DxCx). Dx stands for 'x' dip coating steps. Cx stands for 'x' hours of water annealing. Thus, D1C0 means strawberries that were dip coated only once and that were not exposed to water annealing.

Efficacy of silk fibroin coating in preservation of strawberries freshness was evaluated as a function of coating steps and of silk fibroin crystallinity. The external analysis of the aging of representative strawberries as a function of dip coating steps and of silk polymorphism is presented in FIG. 1. To increasing coating steps and to increasing silk fibroin crystallinity (i.e. longer water annealing process) corresponded a prolonged preservation of strawberries tissues, visible by time dependent reduction in shading from the original red color and maintenance of the original morphology. In addition, increasing coating steps and increasing silk fibroin crystallinity resulted in the downregulation of microbial growth, visible by reduced fungal and mold decay. This was also confirmed by investigation of the time dependent decay of the strawberries' flesh, as shown in FIG. 2. To a higher crystallinity degree of silk fibroin coating corresponded to an enhanced preservation of the internal tissues for the time point considered.

Measurement of Dehydration

Figure 3:
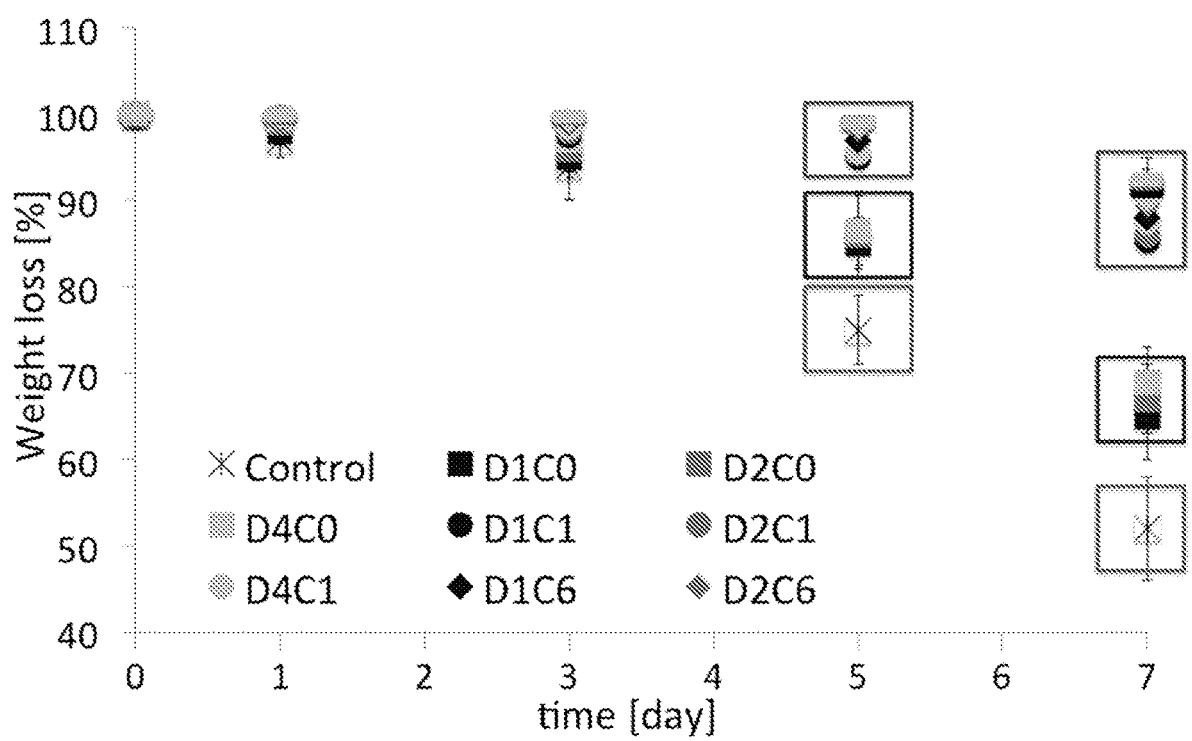
FIG. 3 provides a graph showing weight loss of stored berries as a function of time (over seven days in standard conditions). Berries were stored at 22° C. and 38% RH as received (control) and after coating with silk fibroin solution (DxCx). Dx stands for 'x' dip coating steps. Cx stands for 'x' hours of water annealing. Thus, D1C0 means strawberries that were dip coated only once and that were not exposed to water annealing. Two-ways ANOVA test with Tukey mean analysis was used to evaluate the data. Silk crystallinity but not number of coating steps affected dehydration of the strawberries considered. Uncoated controls lost circa 50 wt % of their original weights in the 7 days considered (highlighted within the red rectangles). Strawberries coated with amorphous silk (DxC0—within the blue rectangles) retained more water compare to controls at days 3 ($p<0.05$). Strawberries coated with crystalline silk further slowed fruit dehydration compared to amorphous coating ($p<0.05$) and to control ($p<0.05$) but no statistical difference was found for different time of water annealing ($p>0.05$).

Dehydration of strawberries is an indication of the breakdown of the red receptacle tissue, which results in off-flavoring, microbial decay, loss of turgor and water evaporation. FIG. 3 shows the time dependent weight loss of strawberry as a function of dip coating steps and of silk fibroin crystallinity degree. Two-ways ANOVA test with Tukey mean analysis was used to evaluate the data. Silk crystallinity but not number of coating steps affected dehydration of the strawberries considered. Uncoated controls lost circa 50 wt % of their original weights in the 7 days considered (highlighted within the red rectangles). Strawberries coated with amorphous silk (D×C0—within the blue rectangles) retained more water compare to controls at days 3 (p<0.05). Strawberries coated with crystalline silk further slowed fruit dehydration compared to amorphous coating (p<0.05) and to control (p<0.05) but no statistical difference was found for different time of water annealing (p>0.05).

Interplay Between Silk Fibroin Thin Membranes and Water

Figures 4A, 4B, 4C:
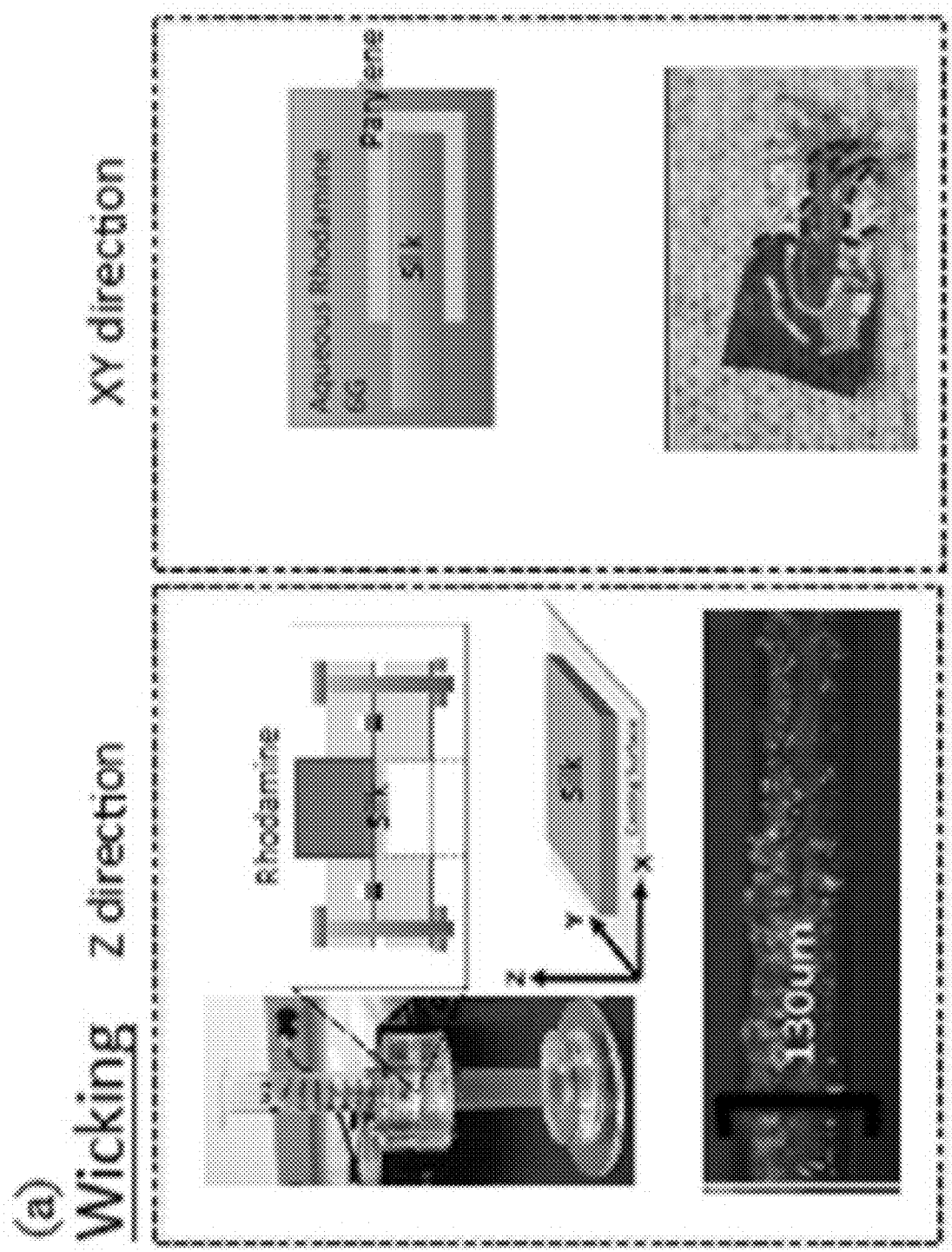
FIGS. 4A-4C depict interplay between water and thin biopolymer membranes.
Figures 4A, 4B, 4C:
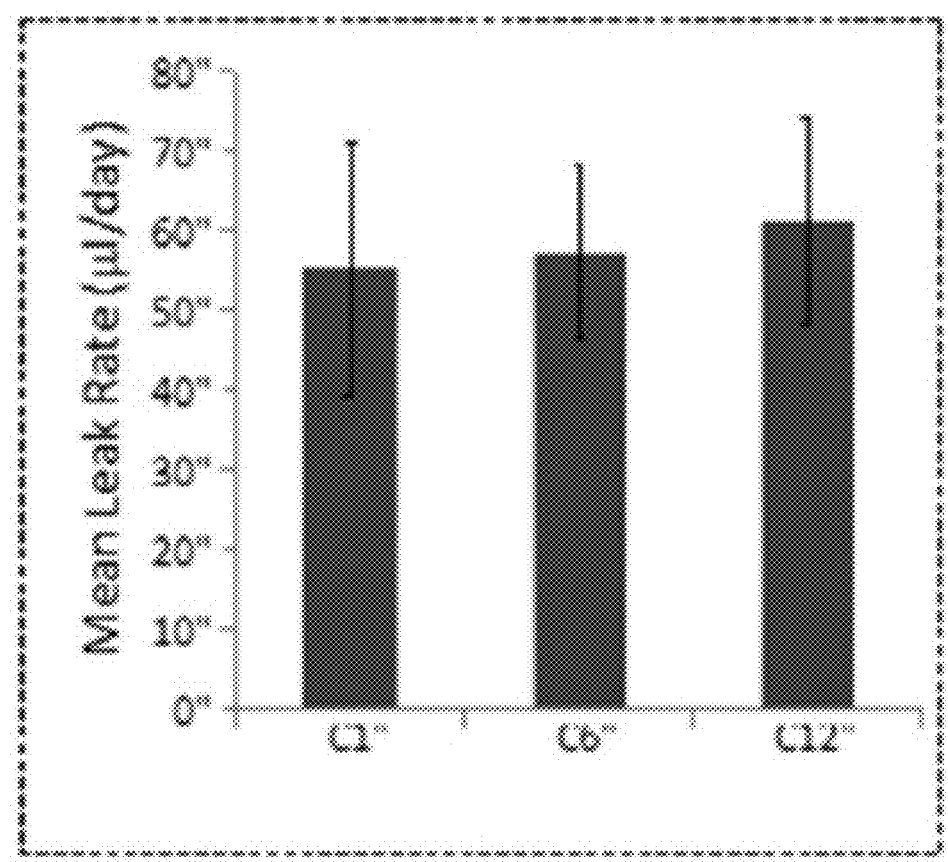
Figures 4A, 4B, 4C:
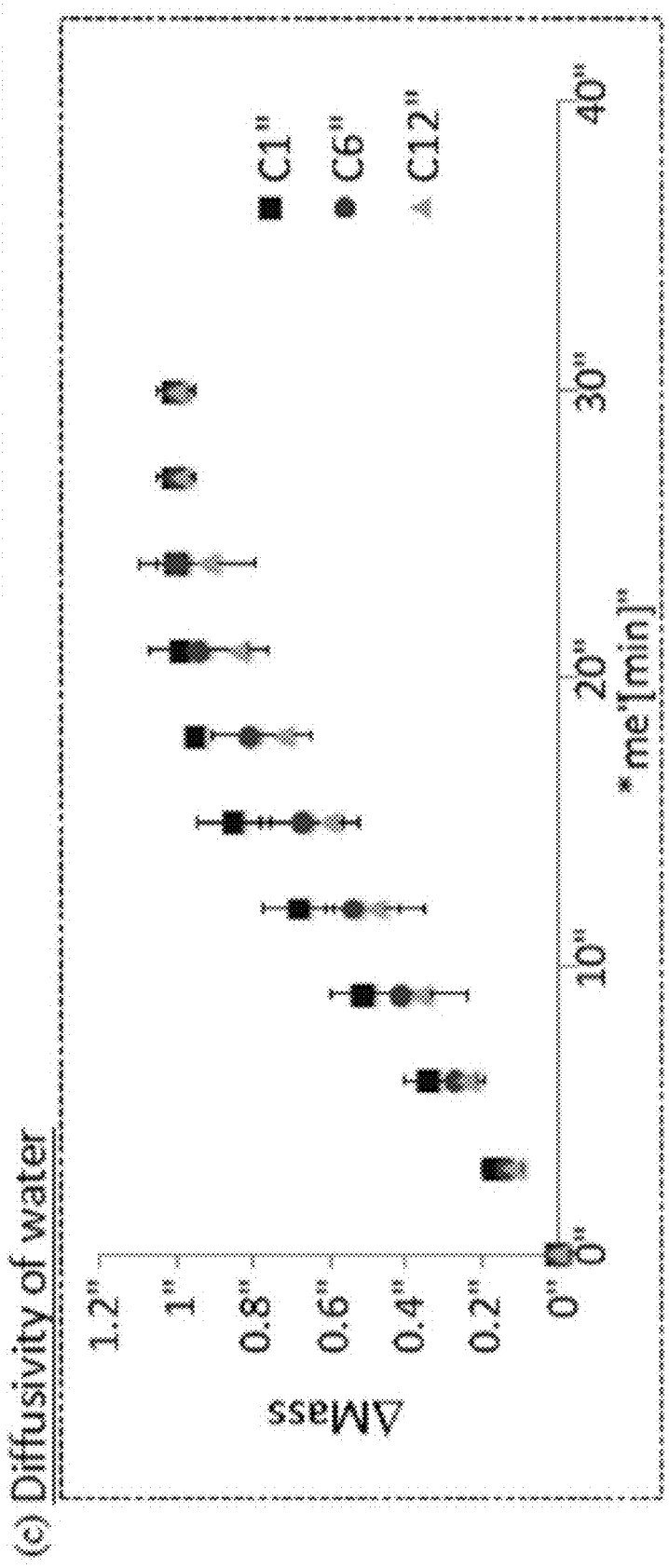

To investigate the phenomenon of fruit dehydration through a thin silk fibroin coating, the interplay between silk fibroin thin membranes and water have been investigated. In particular, wicking, hydrodynamic permeability and water diffusivity phenomena were explored. FIG. 4 shows an evaluation of the interplay between water an thin silk fibroin membranes. For wicking study, silk fibroin crystalline membranes (thickness=130 μm) showed wicking of dyed water in Z and XY direction, indicating the capillary diffusion of water through silk fibroin thin constructs. Investigation of hydrodynamic permeability showed no statistically relevant effect (p<0.05) of silk fibroin crystallinity on water permeation (as per one way ANOVA test with Tukey mean analysis). The study of water diffusivity revealed that crystallinity of silk membranes slightly affected mass transport of water through silk (as per one way ANOVA test with Tukey mean analysis). Table 1 below reports calculated diffusion coefficients for mass transport experiments.

TABLE 1

Diffusion coefficients for mass transport experiments

|     | K             | n           | D (cm$^2$/s)           |
| --- | ------------- | ----------- | ---------------------- |
| C1  | 0.25 ± 0.048  | 0.42 ± 0.04 | 5.79 × 10$^{-6}$       |
| C6  | 0.19          | 0.48 ± 0.03 | 3.21 × 10$^{-6}$       |
| C12 | 0.16          | 0.55 ± 0.02 | 1.05 × 10$^{-6}$       |

Gas Permeability Through Silk Fibroin Membranes

Gas diffusivity through silk fibroin membranes plays a major role in fruit preservation as gases play a major role in fruit stem cells metabolism (e.g., oxygen), are byproducts of their metabolism (e.g., carbon dioxide) and may act as growth factors (e.g., ethylene in climacteric fruit). To evaluate the efficacy of silk fibroin coating as gas barrier, we measured oxygen diffusivity through silk membranes (t=80 μm) of increasing crystallinity. In particular, silk fibroin effective oxygen diffusion coefficient was found to be modulated by protein crystallinity (Table 2).

Table 2 below summarizes changes in calculated effective oxygen diffusion coefficient of silk fibroin membranes, before ("pre-annealing") and after ("post-annealing") crystallization was induced by water annealing tor varying durations of time (e.g., 1-24 hours). For example, when a predominantly amorphous form of silk fibroin was subjected to water annealing for 24 hours to generate a crystalline form of silk, the oxygen effective diffusivity coefficient was decreased by two orders of magnitude. In this particular example, the crystallinity of the annealed silk fibroin was about 55%.

Gas diffusion coefficient of silk fibroin appears to be significantly (e.g., several orders of magnitude) lower than that of edible waxes typically used in the food industry, indicating that silk fibroin-based coatings provide an effective barrier to gas transport, such as oxygen.

TABLE 2

Calculated effective membrane O$_2$ diffusion coefficient and O$_2$ permeability for gas transport experiments (N = 3, RH = 30%)

|           | Film thickness μm | Effective membrane O$_2$ diffusion coefficient [D$_{e,M}$] (steady state) 10$^{-11}$ · (cm$^2$/s) | O$_2$ Permeability [Dk] (steady state) 10$^{-11}$ · mlO$_2$ · cm/(s · cm$^2$ · mmHg) |
| --------- | ----------------- | ------------------------------------------------------------------------------------------------- | ------------------------------------------------------------------------------------ |
| Amorphous | 81 ± 4            | 83.9 ± 7.2                                                                                        | 11.04 ± 0.95                                                                         |
| WA 1 h    | 78 ± 3            | 67.9 ± 3.5                                                                                        | 8.93 ± 0.46                                                                          |
| WA 6 h    | 76 ± 4            | 5.5 ± 1.4                                                                                         | 0.72 ± 0.18                                                                          |
| WA 12 h   | 73 ± 2            | 1.9 ± 0.3                                                                                         | 0.25 ± 0.04                                                                          |
| WA 24 h   | 72 ± 5            | 1.6 ± 0.2                                                                                         | 0.21 ± 0.03                                                                          |

Silk Fibroin as Coating for Climacteric Fruits

Figures 5A, 5B, 5C:
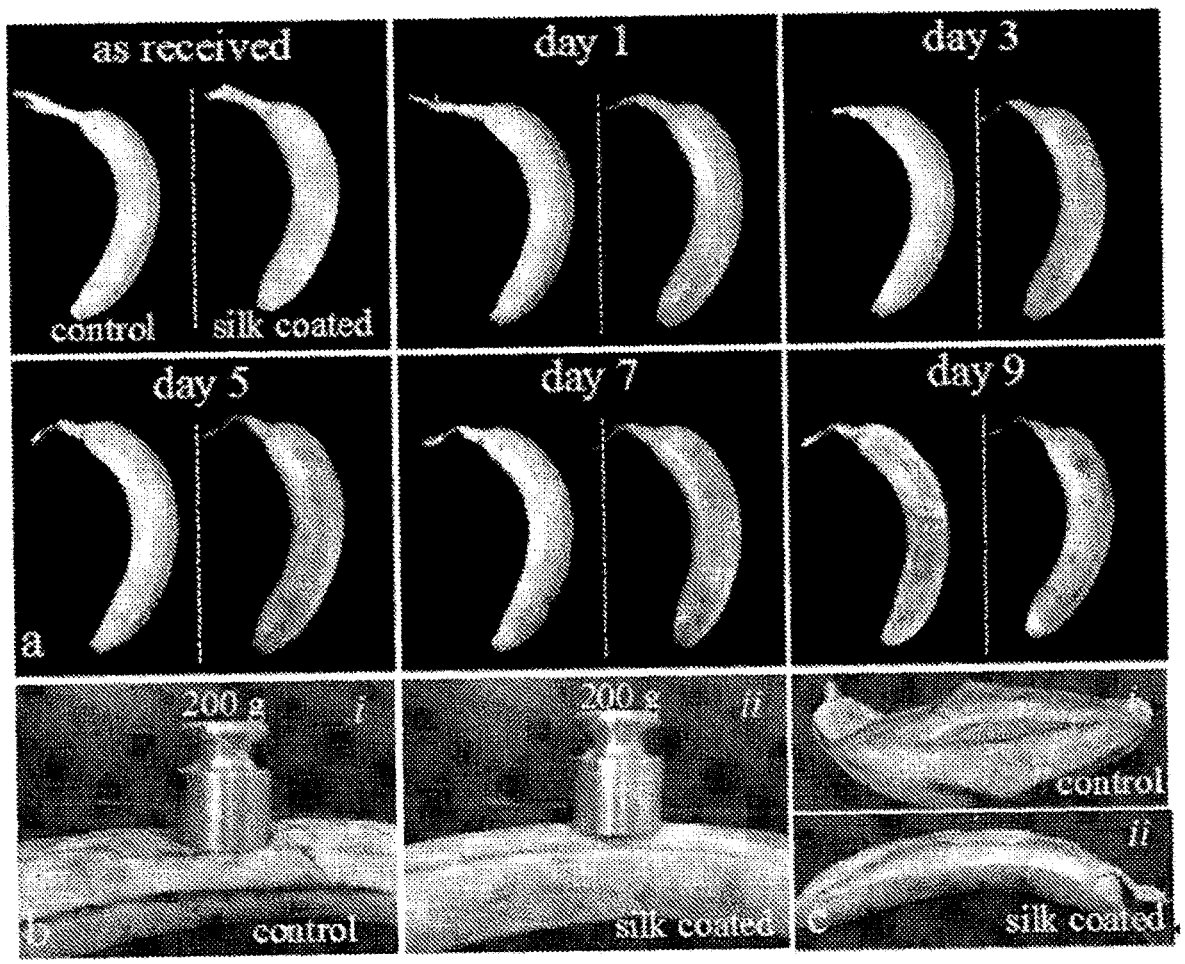
FIGS. 5A-5C provide images of the ripening process of bananas for the evaluation of bananas ripening with and without silk coating. Fruits were stored at 22° C. and 38% RH as received (control) and after coating with crystalline silk fibroin films (silk coated). Bananas were hanged from their respective stem throughout the whole experiment.
Figure 6:
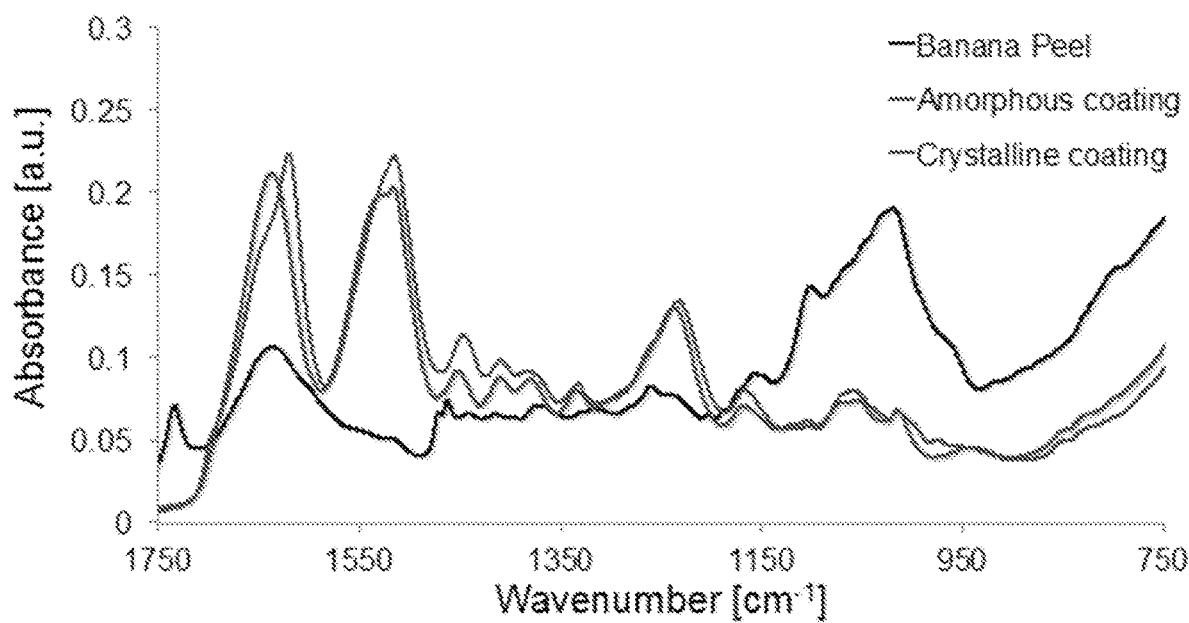
FIG. 6 provides a graph showing chemical characterization of silk fibroin coating on banana's peel. ATR-FTIR was used to investigate silk structure on banana peels' (blue line) upon dip-coating (red line) and upon water annealing for 12 hours (green line).

Fruits that ripen through ethylene production and increased cell respiration are called climacteric. Examples of climacteric fruits are apples, bananas, tomatoes, while berries and grapes are non-climacteric fruits. The climacteric event is associated with changes in fruit color and with the production of sugar in the extracellular space. The efficacy of a silk-based climacteric fruit coating, the ripening of bananas non-coated and coated with silk fibroin was evaluated. FIG. 5 shows an evaluation of bananas ripening with and without a silk coating. Fruits were stored at 22° C. and 38% RH as received (control) and after coating with amorphous or crystalline silk fibroin films (silk coated). Bananas were hanged from their respective stem throughout the whole experiment. Time lapse photography of banana ripening indicating that silk coating decreased the ripening rate. The structure (i.e. amorphous or crystalline) of the fibroin used to coat the climacteric fruit did not affect the fruit ripening (data not shown). Investigation of silk-coated banana turgidity showed that the coating increased the fruit firmness, when compared to uncoated control at day 9 after coating. In addition, morphological analysis of the flesh of non-coated and coated bananas at day 9 post silk coating-treatment revealed a more preserved fruit when the silk coating was applied. Flesh of non-coated banana presented a brown color, while silk-coated fruits preserved a tallow flesh, indication of a decreased ripening rate within the silk-coated sample.

Example 2

Results and Discussion
Silk fibroin as a coating to preserve strawberries freshness.

The thickness of the silk fibroin coating was investigated as a function of number of dip coating processes. Thickness of silk fibroin coating, which was in the range of 27-35 μm, was not statistically significantly influenced (p>0.05) by the number of dip coating steps as shown in below Table 3. The crystallinity of silk fibroin coating was calculated with a previously reported methodology based on the quantification of beta-sheets structures in the Amide III absorbance peak collected with ATR-FTIR spectroscopic analysis and was studied as a function of exposure time to water annealing post process. Conversely as shown in Table 3, the water annealing post process strongly influenced the properties of the silk fibroin coating by increasing the number of beta-sheet structures from 23.2% (for untreated coating) to 58.4% (for coating exposed to water vapor for 12 hours).

TABLE 3

Characterization of edible silk fibroin coating thickness and crystallinity

| Number of dip coating processes in silk fibroin solution [Dx] | Thickness [μm] |
|---|---|
| D1 | 27 ± 8 |
| D6 | 32 ± 7 |
| D12 | 35 ± 8 |

| Exposure time to water annealing post-process [Cx, x = hours] | Silk fibroin edible coating crystallinity [% of beta-sheets] |
|---|---|
| C0 - amorphous | 23.2 ± 1.5 |
| C1 | 36.5 ± 3.3 |
| C6 | 47.6 ± 4.1 |
| C12 | 58.4 ± 4.5 |

Figures 7A, 7B, 7C:
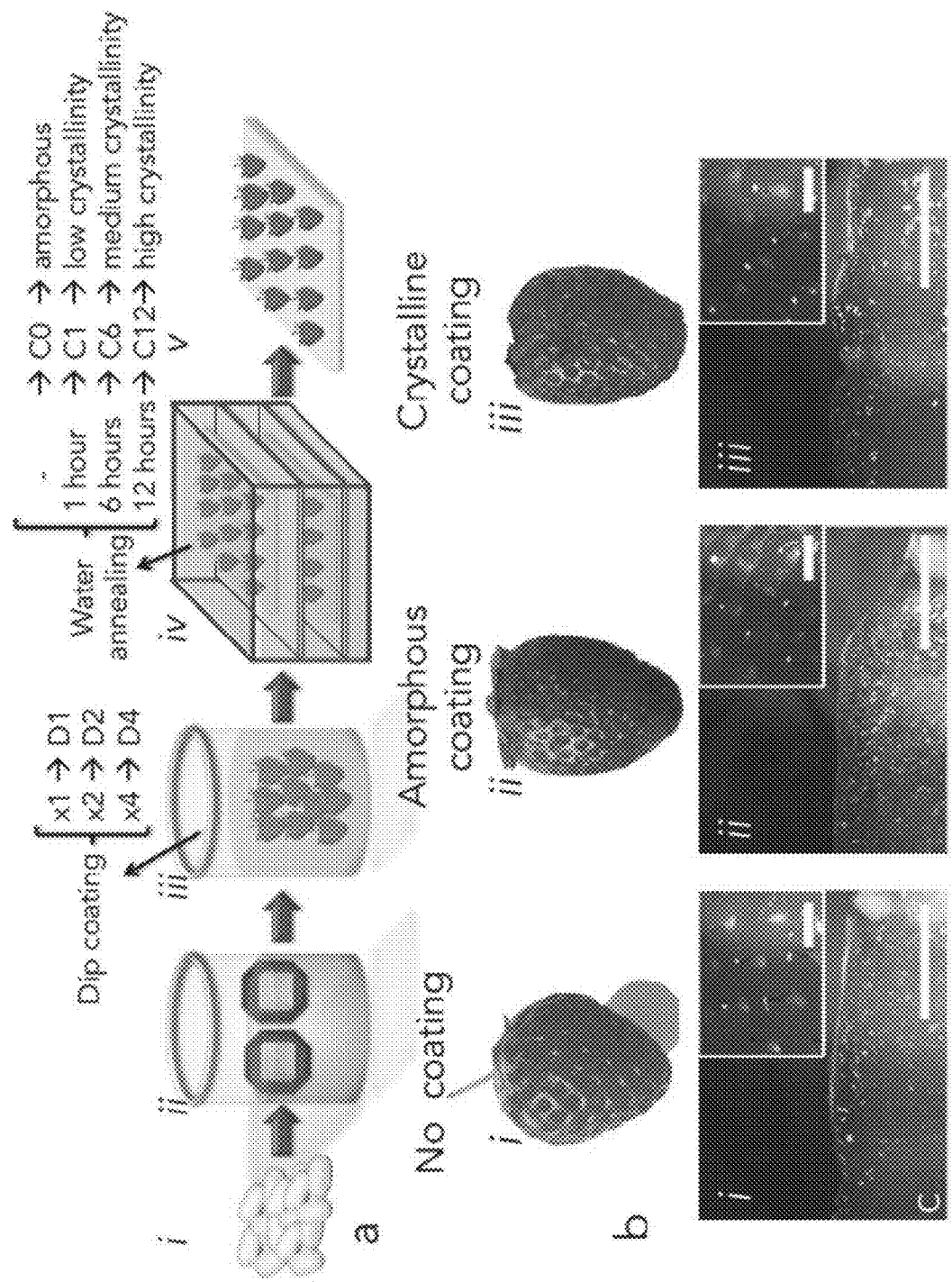
FIGS. 7A-7C show coatings of perishable fruits with edible silk fibroin.
Figures 8A, 8B, 8C:
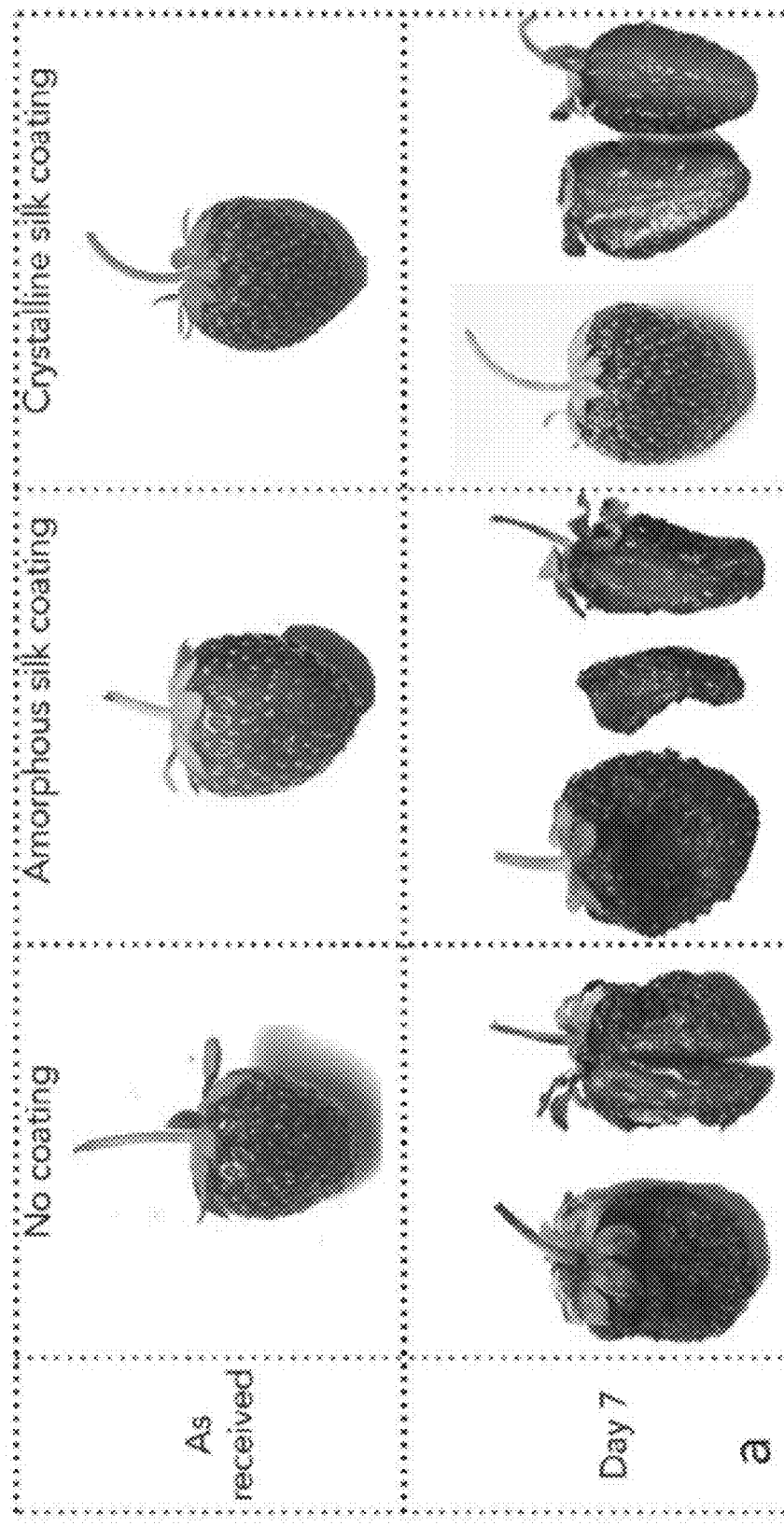
FIGS. 8A-8B show ripening and weight loss of strawberries coated with edible silk fibroin coating.
Figures 8A, 8B, 8C:
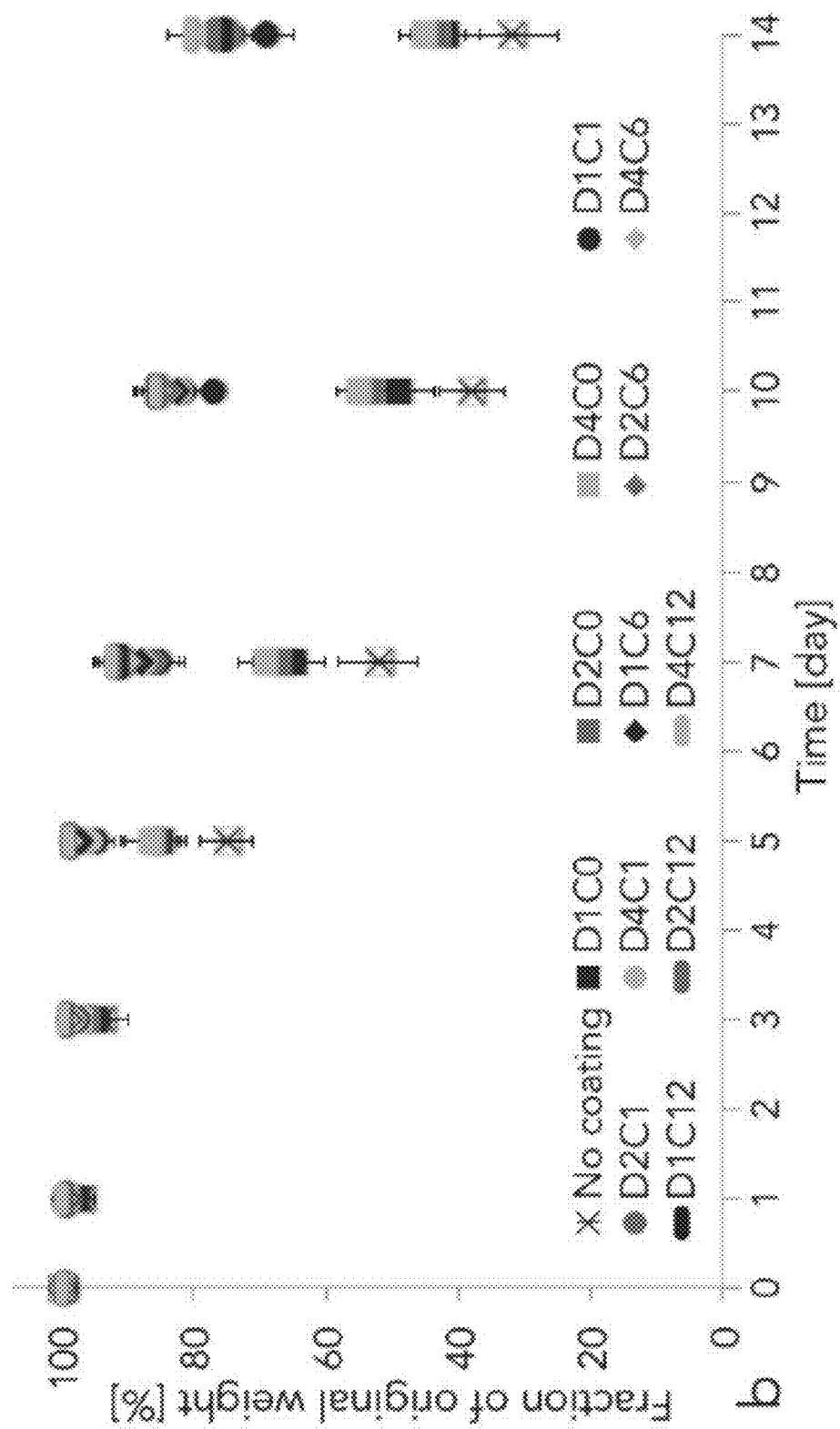

Crystal violet dye was used to main the silk fibroin coating. FIG. 7 at panel (b) shows representative macroscopic images of stained strawberries coated with amorphous and crystalline silk fibroin edible coatings are presented in panel (b) ii and panel (b) iii, respectively. The crystal violet staining is barely visible on the surface of the coated strawberries (black dots) due to the few-micron thickness of the coating. In addition. FIG. 7 at panel (c) shows stereoscopic microscopy of the surface and of the cross-section of crystal violet-stained strawberries coated with, amorphous and crystalline silk fibroin showed no changes in the appearance of the fruit when compared to the uncoated control. The efficacy of silk fibroin edible coating in preserving the freshness of strawberries was evaluated as a function of coating steps and of silk fibroin crystallinity. FIG. 8 shows ripening and weight loss of strawberries coated with edible silk fibroin coating. FIG. 8 at panel (a) shows the external and internal analyses of the aging of representative strawberries as a function of dip coating steps and of silk crystallinity. To increasing coating steps and to increasing silk fibroin crystallinity (i.e. longer water annealing process) corresponded a prolonged preservation of strawberries tissues, visible by time dependent reduction in shading from the original red color and maintenance of the original morphology. In addition, increasing coating steps and increasing silk fibroin crystallinity resulted in the downregulation of microbial growth, visible by reduced fungal and mold decay. This was also confirmed by investigation of the time dependent decay of the strawberries' flesh. To a higher crystallinity degree of silk fibroin coating corresponded an enhanced preservation of the internal tissues for the time point considered.

Measurement of dehydration.

Dehydration of strawberries is an indication of the breakdown of the red receptacle tissue, which results in off-flavoring, microbial decay, loss of turgor and water evaporation. FIG. 8 at panel (b) shows the time dependent weight loss of strawberry as a function of dip coating steps and of silk fibroin crystallinity degree. Two-ways ANOVA test with Tukey mean analysis was used to evaluate the data. Silk crystallinity but not number of coating steps affected dehydration of the strawberries considered. Uncoated controls lost circa 70 wt % of their original weights in the 14 days considered. Strawberries coated with amorphous silk (D×C0) retained more water compare to controls at days 3 (p<0.05). Strawberries coated with crystalline silk further slowed fruit dehydration compared to amorphous coating (p<0.05) and to control (p<0.05) but no statistical difference was found for different time of water annealing (p>0.05).

Interplay between silk fibroin thin membranes and water.

Figures 9A, 9B, 9C:
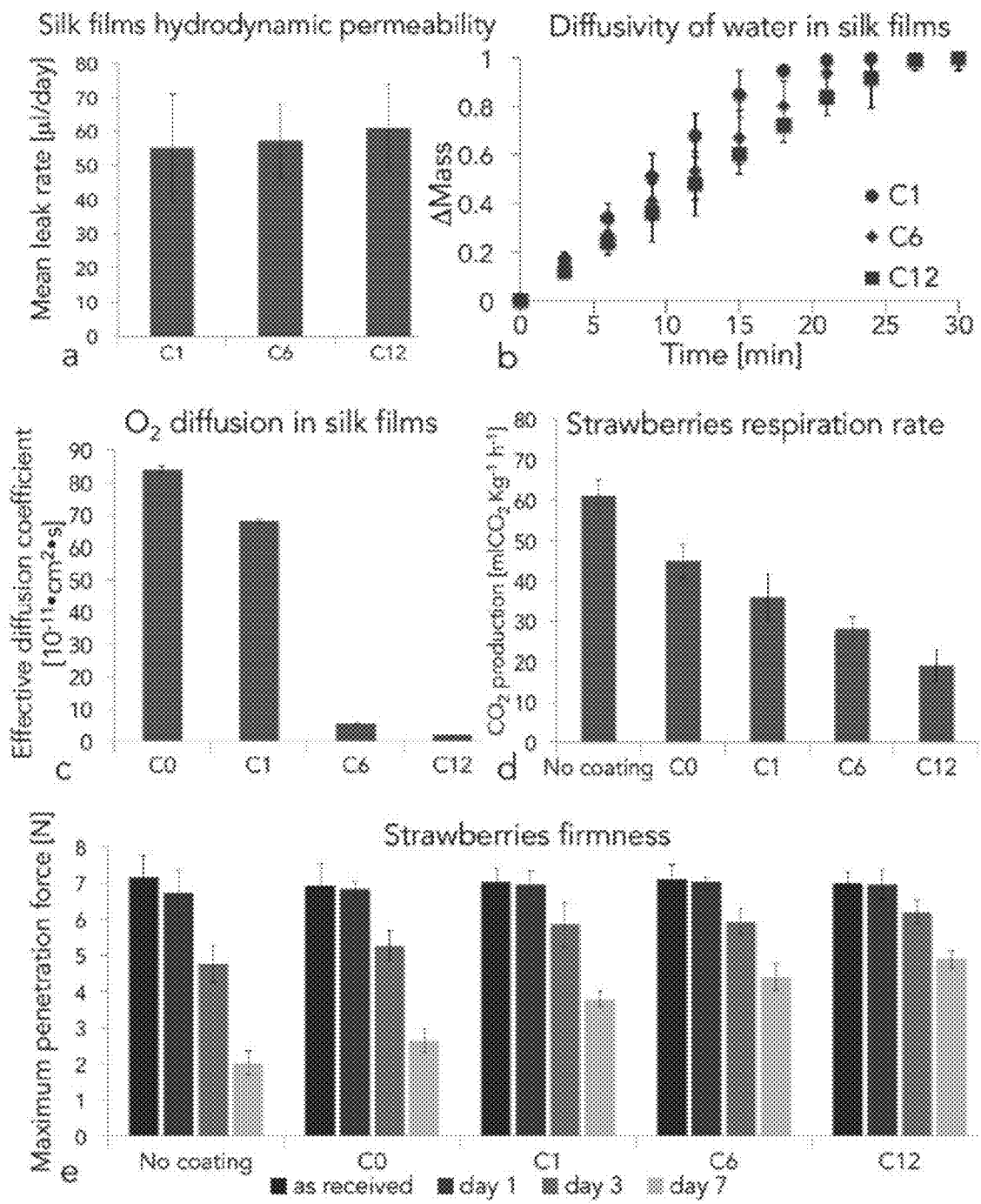

To investigate the phenomenon of fruit dehydration through a thin silk fibroin coating, the interplay between silk fibroin thin membranes and water have been investigated. In particular, FIG. 9 shows permeability and diffusivity of water and oxygen in silk fibroin films as a function of protein crystallinity and their effects on the quality of the edible coating. Hydrodynamic permeability (shown in panel (a)) and water diffusivity phenomena (shown in panel (b)) were explored. Investigation of hydrodynamic permeability showed no statistically relevant effect (p>0.05) of silk fibroin crystallinity on water permeation (as per one way ANOVA test with Tukey mean analysis). The study of water diffusivity revealed that crystallinity of silk membranes slightly affected mass transport of water through silk (as per one way ANOVA test with Tukey mean analysis). Calculated diffusion coefficients for mass transport experiment are below reported in Table 4. k and n are fitting parameters while D is the diffusion coefficient.

TABLE 4

Calculated diffusion coefficients of water for mass transport experiments.

| Silk fibroin edible coating crystallinity | k | n | D (cm$^2$/s) |
|---|---|---|---|
| C1 | 0.25 ± 0.048 | 0.42 ± 0.04 | 5.79 × 10$^{-6}$ |
| C6 | 0.19 | 0.48 ± 0.03 | 3.21 × 10$^{-6}$ |
| C12 | 0.16 | 0.55 ± 0.02 | 1.05 × 10$^{-6}$ |

Gas diffusivity through silk membranes.

Gas diffusivity through silk fibroin membranes plays a major role in fruit presentation as gases play a major role in fruit stem cells metabolism (i.e. oxygen), are byproducts of their metabolism (i.e. carbon dioxide) and may act as growth factors (i.e. ethylene in climacteric fruit). To evaluate the efficacy of silk fibroin coating as gas barrier. FIG. 9 at panel (c) and below Table 5 show measured oxygen diffusivity through silk membranes (t=70-80 μm) of increasing crystallinity. In particular, silk fibroin effective oxygen diffusion coefficient was found to be modulated by protein crystallinity, as a decreased of two orders of magnitude in the oxygen effective diffusivity coefficient was calculated between amorphous and 58.4% crystalline silk (12 hours of water annealing).

TABLE 5

Calculated effective silk fibroin $O_2$ diffusion coefficient for gas transport experiments.

| Silk fibroin edible coating crystallinity | Film thickness μm | Effective membrane $O_2$ diffusion coefficient $[D_{e,M}]$ (steady state) $10^{-11} \cdot (cm^2/s)$ |
|---|---|---|
| C0- amorphous | 81 ± 4 | 83.9 ± 7.2 |
| C1 | 78 ± 3 | 67.9 ± 3.5 |
| C6 | 76 ± 4 | 5.5 ± 1.4 |
| C12 | 73 ± 2 | 1.9 ± 0.3 |

Respiration rate in silk fibroin coated strawberries.

Respiration rate is an important parameter to evaluate the metabolic activity of the stem cells present in the fruits. The higher the respiration rate, the higher the metabolic activity and the faster the fruit decay. FIG. 9 at panel (d) shows the respiration rate of silk-coated strawberries that was measured as a function of coating crystallinity. To higher crystallinity degrees corresponded a statistically significant decrease in the production of $CO_2$ ($p<0.05$), which indicated a decrease in the respiration rate of the fruit. It was evident the crystallinity degree of the edible silk fibroin coating controlled the exchange of the gases between the strawberry and the environment due to the strong influence that silk polymorphism has on the permeability to gases like $CO_2$ and $O_2$.

Firmness rate in silk fibroin-coated strawberries.

FIG. 9 at panel (e) shows a puncture (or penetration) test was used to evaluate the effects of silk coating on the firmness of strawberries as a function of storage time and of coating crystallinity. While natural decay of the strawberries caused a decrease in the fruit firmness, as measure by a time-dependent decrease in the force required to penetrate the fruit ($p<0.05$), an increase in the coating crystallinity corresponded to a statistically significant delay in the decay of the fruit firmness at days 3 and 7.

Silk fibroin as coating for climacteric fruits.

Figures 10A, 10B, 10C:
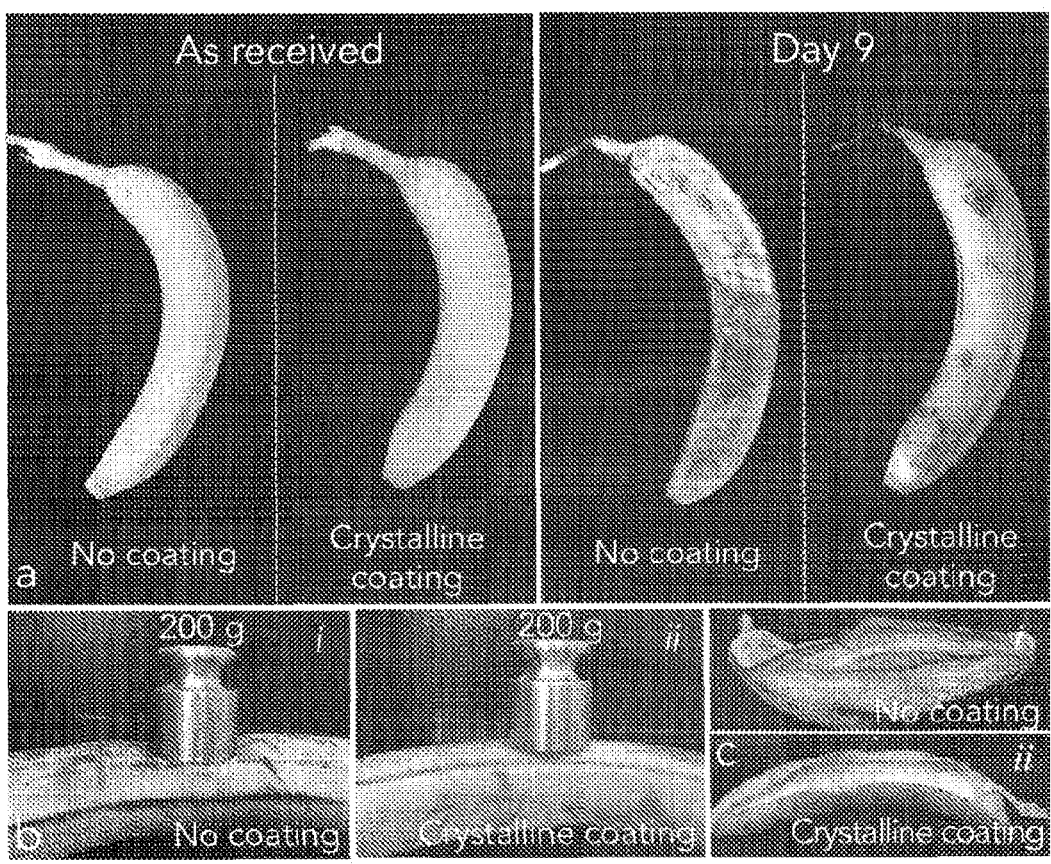
FIGS. 10A-10C show an evaluation of bananas ripening with and without crystalline silk coating. Fruits were stored at 22° C. and 38% RH as received (no coating) and after coating with crystalline silk fibroin films (Crystalline coating). Bananas were hanged from their respective stem throughout the whole experiment.

Fruits that ripen through ethylene production and increased cell respiration are called climacteric. Examples of climacteric fruits are apples, bananas, tomatoes, while berries and grapes are non-climacteric fruits. The climacteric event is associated with changes in fruit color and with the production of sugar in the extracellular space. FIG. 10 shows an evaluation of the efficacy of a silk-based climacteric fruit coating, the ripening of bananas non-coated and coated with silk fibroin. Fruits were stored at 22° C. and 38% RH as received (No coating) and after coating with crystalline silk fibroin films (Crystalline coating). Bananas were suspended from their respective stem throughout the whole experiment. Time-lapse photography of banana ripening indicating that silk coating decreased the ripening rate. The structure (i.e. amorphous or crystalline) of the fibroin used to coat the climacteric fruit did not affect the fruit ripening (data not shown). Investigation of silk-coated banana turgidity showed that the coating increased the fruit firmness, when compared to uncoated control at day 9 after coating. In addition, morphological analysis of the flesh of non-coated and coated bananas at day 9 post silk coating-treatment revealed a more preserved fruit when the silk coating was applied. Flesh of non-coated banana presented a brown color, while silk-coated fruits preserved a tallow flesh, indication of a decreased ripening rate within the silk-coated sample.

Silk fibroin is an effective coating to enhance freshness of perishable food. Silk polymorphism may be used to tailor the properties of the coating, affecting the interplay between silk fibroin and water evaporation and the microbial-driven food decay.

Conclusion

Silk fibroin is an effective coating to enhance freshness of perishable food. Silk polymorphism may be used to tailor the properties of the coating, affecting the interplay between silk fibroin and water evaporation and the microbial-driven food decay.

OTHER EMBODIMENTS AND EQUIVALENTS

While the present disclosure has explicitly discussed certain particular embodiments and examples of the present disclosure, those skilled in the art will appreciate that the invention is not intended to be limited to such embodiments or examples. On the contrary, the present disclosure encompasses various alternatives, modifications, and equivalents of such particular embodiments and/or example, as will be appreciated by those of skill in the art.

Accordingly, for example, methods and diagrams of should not be read as limited to a particular described order or arrangement of steps or elements unless explicitly stated or clearly required from context (e.g., otherwise inoperable). Furthermore, different features of particular elements that may be exemplified in different embodiments may be combined with one another in some embodiments.

We claim:

1. A product comprising a packaging item and a coating, wherein at least a portion of the coating is in contact with at least a portion of the packaging item; wherein the coating comprises an amphiphilic polypeptide and wherein the coating comprises a first crystallinity degree which is higher than a second crystallinity degree; the first crystallinity degree having been produced by an annealing process, a crosslinking process, or a combination thereof applied to the coating after at least a portion of the coating was in contact with the packaging item; and the second crystallinity degree being a crystallinity degree of the coating prior to the annealing process, the crosslinking process, or a combination thereof.

2. The product of claim 1, wherein the amphiphilic polypeptide comprises an amorphous fraction and a crystalline fraction.

3. The product of claim 2, wherein the amorphous fraction is or comprises random coil structure, and wherein the crystalline fraction is or comprises a domain of a protein or derivative thereof that forms a beta-sheet structure.

4. The product of claim 3, wherein the protein is selected from the group consisting of: fibroins, actins, collagens, catenins, claudins, coilins, elastins, elaunins, extensins, fibrillins, lamins, laminins, keratins, tublins, viral structural proteins, zein proteins, and any combinations thereof.

5. The product of claim 1, wherein the packaging item is packaging for a perishable item.

6. The product of claim 5, wherein the packaging is selected from a wrap, a cover, and a bottle.

7. The product of claim 1, wherein at least 65% of amino acids of the amphiphilic polypeptide are in the crystalline fraction.

8. The product of claim 1, wherein at least one surface of the packaging item is in direct contact with the coating.

9. The product of claim 1, wherein the coating has a water diffusivity of less than $10^{-6}$ cm$^2$/s.

10. The product of claim 1, wherein the coating provides an oxygen permeability coefficient ($Dk_{O2}$) of less than $10^{-10}$ [ml$_{O2}$·cm)/(cm·s·mmHg)].

11. The product of claim 1, wherein the coating is transparent.

12. The product of claim 1, wherein the coating further comprises an additive.

13. The product of claim 12, wherein the additive is selected from the group consisting of: anti-microbial agents, antifungal agents, antibacterial agents, enzyme inhibitors, ethylene-capturing molecules, ethylene-absorbing agents, aluminosilicates, silk fibroin-based aerogels, oxidizing agents, potassium permanganate, ethylene receptor antagonists, porphyrins, hormones, hormone receptor agonists, hormone receptor antagonists, nutraceutical agents, dietary supplements, flavorings, sweeteners, perfumes, fragrances, colorings, and dyes, and any combinations thereof.

\* \* \* \* \*

SEQUENCE LISTING

```
<160> NUMBER OF SEQ ID NOS: 25

<210> SEQ ID NO 1
<211> LENGTH: 90
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(90)
<223> OTHER INFORMATION: This sequence may encompass 5-15 'Gly Ala Gly
      Ala Gly Ser' repeating units.
<220> FEATURE:
<221> NAME/KEY: MISC_FEATURE
<222> LOCATION: (31)..(90)
```

```
<223> OTHER INFORMATION: Any one or more repeat of "Gly Ala Gly Ala Gly
      Ser" or all repeats of "Gly Ala Gly Ala Gly Ser" in amino acids
      31-90 can either be present or absent.

<400> SEQUENCE: 1

Gly Ala Gly Ala Gly Ser Gly Ala Gly Ala Gly Ser Gly Ala Gly Ala
1               5                  10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser
                85                  90

<210> SEQ ID NO 2
<211> LENGTH: 30
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(30)
<223> OTHER INFORMATION: This sequence may encompass 5-15 "Gly Xaa"
      repeating units.
<220> FEATURE:
<221> NAME/KEY: MOD_RES
<222> LOCATION: (2)..(2)
<223> OTHER INFORMATION: Val, Ile or Ala
<220> FEATURE:
<221> NAME/KEY: MOD_RES
<222> LOCATION: (4)..(4)
<223> OTHER INFORMATION: Val, Ile or Ala
<220> FEATURE:
<221> NAME/KEY: MOD_RES
<222> LOCATION: (6)..(6)
<223> OTHER INFORMATION: Val, Ile or Ala
<220> FEATURE:
<221> NAME/KEY: MOD_RES
<222> LOCATION: (8)..(8)
<223> OTHER INFORMATION: Val, Ile or Ala
<220> FEATURE:
<221> NAME/KEY: MOD_RES
<222> LOCATION: (10)..(10)
<223> OTHER INFORMATION: Val, Ile or Ala
<220> FEATURE:
<221> NAME/KEY: MISC_FEATURE
<222> LOCATION: (11)..(30)
<223> OTHER INFORMATION: Any one or more repeat of "Gly Xaa" or all
      repeats of "Gly Xaa" in amino acids 11-30 can either be present or
      absent
<220> FEATURE:
<221> NAME/KEY: MOD_RES
<222> LOCATION: (12)..(12)
<223> OTHER INFORMATION: Val, Ile or Ala
<220> FEATURE:
<221> NAME/KEY: MOD_RES
<222> LOCATION: (14)..(14)
<223> OTHER INFORMATION: Val, Ile or Ala
<220> FEATURE:
<221> NAME/KEY: MOD_RES
<222> LOCATION: (16)..(16)
<223> OTHER INFORMATION: Val, Ile or Ala
<220> FEATURE:
<221> NAME/KEY: MOD_RES
<222> LOCATION: (18)..(18)
<223> OTHER INFORMATION: Val, Ile or Ala
<220> FEATURE:
```

```
<221> NAME/KEY: MOD_RES
<222> LOCATION: (20)..(20)
<223> OTHER INFORMATION: Val, Ile or Ala
<220> FEATURE:
<221> NAME/KEY: MOD_RES
<222> LOCATION: (22)..(22)
<223> OTHER INFORMATION: Val, Ile or Ala
<220> FEATURE:
<221> NAME/KEY: MOD_RES
<222> LOCATION: (24)..(24)
<223> OTHER INFORMATION: Val, Ile or Ala
<220> FEATURE:
<221> NAME/KEY: MOD_RES
<222> LOCATION: (26)..(26)
<223> OTHER INFORMATION: Val, Ile or Ala
<220> FEATURE:
<221> NAME/KEY: MOD_RES
<222> LOCATION: (28)..(28)
<223> OTHER INFORMATION: Val, Ile or Ala
<220> FEATURE:
<221> NAME/KEY: MOD_RES
<222> LOCATION: (30)..(30)
<223> OTHER INFORMATION: Val, Ile or Ala

<400> SEQUENCE: 2

Gly Xaa Gly Xaa Gly Xaa Gly Xaa Gly Xaa Gly Xaa Gly Xaa Gly Xaa
1               5                   10                  15

Gly Xaa Gly Xaa Gly Xaa Gly Xaa Gly Xaa Gly Xaa Gly Xaa
            20                  25                  30

<210> SEQ ID NO 3
<211> LENGTH: 4
<212> TYPE: PRT
<213> ORGANISM: Artificial Sequence
<220> FEATURE:
<223> OTHER INFORMATION: synthetic

<400> SEQUENCE: 3

Gly Ala Ala Ser
1

<210> SEQ ID NO 4
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: Ser or absent
<220> FEATURE:
<221> NAME/KEY: MOD_RES
<222> LOCATION: (14)..(15)
<223> OTHER INFORMATION: Ala or absent

<400> SEQUENCE: 4

Ser Xaa Ala Ala Ala Ala Ala Ala Ala Ala Ala Ala Ala Xaa Xaa
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(5)
<223> OTHER INFORMATION: Any amino acid, and any one or all of amino
      acids 2-5 can be absent or present.
<220> FEATURE:
```

```
<221> NAME/KEY: MOD_RES
<222> LOCATION: (8)..(8)
<223> OTHER INFORMATION: Any amino acid

<400> SEQUENCE: 5

Gly Xaa Xaa Xaa Xaa Gly Gly Xaa
1               5

<210> SEQ ID NO 6
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(4)
<223> OTHER INFORMATION: Ala, Ser, Tyr, Arg, Asp, Val or Trp

<400> SEQUENCE: 6

Gly Gly Gly Xaa
1

<210> SEQ ID NO 7
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(12)
<223> OTHER INFORMATION: This sequence may encompass 1-2 "(Ser)1-2
      (Ala)1-4" repeating units.
<220> FEATURE:
<221> NAME/KEY: MOD_RES
<222> LOCATION: (2)..(2)
<223> OTHER INFORMATION: Ser or absent
<220> FEATURE:
<221> NAME/KEY: MOD_RES
<222> LOCATION: (4)..(6)
<223> OTHER INFORMATION: Ala or absent
<220> FEATURE:
<221> NAME/KEY: MOD_RES
<222> LOCATION: (7)..(12)
<223> OTHER INFORMATION: Any one or all of amino acids 7-12 can either
      be absent or present.
<220> FEATURE:
<221> NAME/KEY: MOD_RES
<222> LOCATION: (8)..(8)
<223> OTHER INFORMATION: Ser or absent
<220> FEATURE:
<221> NAME/KEY: MOD_RES
<222> LOCATION: (10)..(12)
<223> OTHER INFORMATION: Ala or absent

<400> SEQUENCE: 7

Ser Xaa Ala Xaa Xaa Xaa Ser Xaa Ala Xaa Xaa Xaa
1               5                   10

<210> SEQ ID NO 8
<211> LENGTH: 6
<212> TYPE: PRT
<213> ORGANISM: Artificial Sequence
<220> FEATURE:
<223> OTHER INFORMATION: synthetic

<400> SEQUENCE: 8

Gly Leu Gly Gly Leu Gly
1               5
```

```
<210> SEQ ID NO 9
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: Leu, Ile, Val or Pro
<220> FEATURE:
<221> NAME/KEY: MOD_RES
<222> LOCATION: (5)..(5)
<223> OTHER INFORMATION: Leu, Ile, Val or Pro

<400> SEQUENCE: 9

Gly Xaa Gly Gly Xaa Gly
1               5

<210> SEQ ID NO 10
<211> LENGTH: 300
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(300)
<223> OTHER INFORMATION: This sequence may encompass 3-20 'Gly Pro (Gly
      Gly Xaa)1-4 Tyr)' repeating units.
<220> FEATURE:
<221> NAME/KEY: MISC_FEATURE
<222> LOCATION: (3)..(14)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (5)..(5)
<223> OTHER INFORMATION: Tyr, Val, Ser or Ala
<220> FEATURE:
<221> NAME/KEY: MOD_RES
<222> LOCATION: (8)..(8)
<223> OTHER INFORMATION: Tyr, Val, Ser or Ala
<220> FEATURE:
<221> NAME/KEY: MOD_RES
<222> LOCATION: (11)..(11)
<223> OTHER INFORMATION: Tyr, Val, Ser or Ala
<220> FEATURE:
<221> NAME/KEY: MOD_RES
<222> LOCATION: (14)..(14)
<223> OTHER INFORMATION: Tyr, Val, Ser or Ala
<220> FEATURE:
<221> NAME/KEY: MISC_FEATURE
<222> LOCATION: (18)..(29)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (20)..(20)
<223> OTHER INFORMATION: Tyr, Val, Ser or Ala
<220> FEATURE:
<221> NAME/KEY: MOD_RES
<222> LOCATION: (23)..(23)
<223> OTHER INFORMATION: Tyr, Val, Ser or Ala
<220> FEATURE:
<221> NAME/KEY: MOD_RES
<222> LOCATION: (26)..(26)
<223> OTHER INFORMATION: Tyr, Val, Ser or Ala
<220> FEATURE:
<221> NAME/KEY: MOD_RES
<222> LOCATION: (29)..(29)
<223> OTHER INFORMATION: Tyr, Val, Ser or Ala
<220> FEATURE:
<221> NAME/KEY: MISC_FEATURE
<222> LOCATION: (33)..(44)
```

```
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (35)..(35)
<223> OTHER INFORMATION: Tyr, Val, Ser or Ala
<220> FEATURE:
<221> NAME/KEY: MOD_RES
<222> LOCATION: (38)..(38)
<223> OTHER INFORMATION: Tyr, Val, Ser or Ala
<220> FEATURE:
<221> NAME/KEY: MOD_RES
<222> LOCATION: (41)..(41)
<223> OTHER INFORMATION: Tyr, Val, Ser or Ala
<220> FEATURE:
<221> NAME/KEY: MOD_RES
<222> LOCATION: (44)..(44)
<223> OTHER INFORMATION: Tyr, Val, Ser or Ala
<220> FEATURE:
<221> NAME/KEY: MISC_FEATURE
<222> LOCATION: (46)..(300)
<223> OTHER INFORMATION: Any one or more repeat of 'Gly Pro (Gly Gly
      Xaa)1-4 Tyr)' or all repeats of 'Gly Pro (Gly Gly Xaa)1-4 Tyr)' in
      amino acids 46-300 can either be present or absent.
<220> FEATURE:
<221> NAME/KEY: MISC_FEATURE
<222> LOCATION: (48)..(59)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (50)..(50)
<223> OTHER INFORMATION: Tyr, Val, Ser or Ala
<220> FEATURE:
<221> NAME/KEY: MOD_RES
<222> LOCATION: (53)..(53)
<223> OTHER INFORMATION: Tyr, Val, Ser or Ala
<220> FEATURE:
<221> NAME/KEY: MOD_RES
<222> LOCATION: (56)..(56)
<223> OTHER INFORMATION: Tyr, Val, Ser or Ala
<220> FEATURE:
<221> NAME/KEY: MOD_RES
<222> LOCATION: (59)..(59)
<223> OTHER INFORMATION: Tyr, Val, Ser or Ala
<220> FEATURE:
<221> NAME/KEY: MISC_FEATURE
<222> LOCATION: (63)..(74)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (65)..(65)
<223> OTHER INFORMATION: Tyr, Val, Ser or Ala
<220> FEATURE:
<221> NAME/KEY: MOD_RES
<222> LOCATION: (68)..(68)
<223> OTHER INFORMATION: Tyr, Val, Ser or Ala
<220> FEATURE:
<221> NAME/KEY: MOD_RES
<222> LOCATION: (71)..(71)
<223> OTHER INFORMATION: Tyr, Val, Ser or Ala
<220> FEATURE:
<221> NAME/KEY: MOD_RES
<222> LOCATION: (74)..(74)
<223> OTHER INFORMATION: Tyr, Val, Ser or Ala
<220> FEATURE:
<221> NAME/KEY: MISC_FEATURE
<222> LOCATION: (78)..(89)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (80)..(80)
<223> OTHER INFORMATION: Tyr, Val, Ser or Ala
```

```
<220> FEATURE:
<221> NAME/KEY: MOD_RES
<222> LOCATION: (83)..(83)
<223> OTHER INFORMATION: Tyr, Val, Ser or Ala
<220> FEATURE:
<221> NAME/KEY: MOD_RES
<222> LOCATION: (86)..(86)
<223> OTHER INFORMATION: Tyr, Val, Ser or Ala
<220> FEATURE:
<221> NAME/KEY: MOD_RES
<222> LOCATION: (89)..(89)
<223> OTHER INFORMATION: Tyr, Val, Ser or Ala
<220> FEATURE:
<221> NAME/KEY: MISC_FEATURE
<222> LOCATION: (93)..(104)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (95)..(95)
<223> OTHER INFORMATION: Tyr, Val, Ser or Ala
<220> FEATURE:
<221> NAME/KEY: MOD_RES
<222> LOCATION: (98)..(98)
<223> OTHER INFORMATION: Tyr, Val, Ser or Ala
<220> FEATURE:
<221> NAME/KEY: MOD_RES
<222> LOCATION: (101)..(101)
<223> OTHER INFORMATION: Tyr, Val, Ser or Ala
<220> FEATURE:
<221> NAME/KEY: MOD_RES
<222> LOCATION: (104)..(104)
<223> OTHER INFORMATION: Tyr, Val, Ser or Ala
<220> FEATURE:
<221> NAME/KEY: MISC_FEATURE
<222> LOCATION: (108)..(119)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (110)..(110)
<223> OTHER INFORMATION: Tyr, Val, Ser or Ala
<220> FEATURE:
<221> NAME/KEY: MOD_RES
<222> LOCATION: (113)..(113)
<223> OTHER INFORMATION: Tyr, Val, Ser or Ala
<220> FEATURE:
<221> NAME/KEY: MOD_RES
<222> LOCATION: (116)..(116)
<223> OTHER INFORMATION: Tyr, Val, Ser or Ala
<220> FEATURE:
<221> NAME/KEY: MOD_RES
<222> LOCATION: (119)..(119)
<223> OTHER INFORMATION: Tyr, Val, Ser or Ala
<220> FEATURE:
<221> NAME/KEY: MISC_FEATURE
<222> LOCATION: (123)..(134)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (125)..(125)
<223> OTHER INFORMATION: Tyr, Val, Ser or Ala
<220> FEATURE:
<221> NAME/KEY: MOD_RES
<222> LOCATION: (128)..(128)
<223> OTHER INFORMATION: Tyr, Val, Ser or Ala
<220> FEATURE:
<221> NAME/KEY: MOD_RES
<222> LOCATION: (131)..(131)
<223> OTHER INFORMATION: Tyr, Val, Ser or Ala
<220> FEATURE:
<221> NAME/KEY: MOD_RES
<222> LOCATION: (134)..(134)
<223> OTHER INFORMATION: Tyr, Val, Ser or Ala
<220> FEATURE:
```

```
<221> NAME/KEY: MISC_FEATURE
<222> LOCATION: (138)..(149)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (140)..(140)
<223> OTHER INFORMATION: Tyr, Val, Ser or Ala
<220> FEATURE:
<221> NAME/KEY: MOD_RES
<222> LOCATION: (143)..(143)
<223> OTHER INFORMATION: Tyr, Val, Ser or Ala
<220> FEATURE:
<221> NAME/KEY: MOD_RES
<222> LOCATION: (146)..(146)
<223> OTHER INFORMATION: Tyr, Val, Ser or Ala
<220> FEATURE:
<221> NAME/KEY: MOD_RES
<222> LOCATION: (149)..(149)
<223> OTHER INFORMATION: Tyr, Val, Ser or Ala
<220> FEATURE:
<221> NAME/KEY: MISC_FEATURE
<222> LOCATION: (153)..(164)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (155)..(155)
<223> OTHER INFORMATION: Tyr, Val, Ser or Ala
<220> FEATURE:
<221> NAME/KEY: MOD_RES
<222> LOCATION: (158)..(158)
<223> OTHER INFORMATION: Tyr, Val, Ser or Ala
<220> FEATURE:
<221> NAME/KEY: MOD_RES
<222> LOCATION: (161)..(161)
<223> OTHER INFORMATION: Tyr, Val, Ser or Ala
<220> FEATURE:
<221> NAME/KEY: MOD_RES
<222> LOCATION: (164)..(164)
<223> OTHER INFORMATION: Tyr, Val, Ser or Ala
<220> FEATURE:
<221> NAME/KEY: MISC_FEATURE
<222> LOCATION: (168)..(179)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (170)..(170)
<223> OTHER INFORMATION: Tyr, Val, Ser or Ala
<220> FEATURE:
<221> NAME/KEY: MOD_RES
<222> LOCATION: (173)..(173)
<223> OTHER INFORMATION: Tyr, Val, Ser or Ala
<220> FEATURE:
<221> NAME/KEY: MOD_RES
<222> LOCATION: (176)..(176)
<223> OTHER INFORMATION: Tyr, Val, Ser or Ala
<220> FEATURE:
<221> NAME/KEY: MOD_RES
<222> LOCATION: (179)..(179)
<223> OTHER INFORMATION: Tyr, Val, Ser or Ala
<220> FEATURE:
<221> NAME/KEY: MISC_FEATURE
<222> LOCATION: (183)..(194)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (185)..(185)
<223> OTHER INFORMATION: Tyr, Val, Ser or Ala
<220> FEATURE:
<221> NAME/KEY: MOD_RES
<222> LOCATION: (188)..(188)
<223> OTHER INFORMATION: Tyr, Val, Ser or Ala
```

-continued

```
<220> FEATURE:
<221> NAME/KEY: MOD_RES
<222> LOCATION: (191)..(191)
<223> OTHER INFORMATION: Tyr, Val, Ser or Ala
<220> FEATURE:
<221> NAME/KEY: MOD_RES
<222> LOCATION: (194)..(194)
<223> OTHER INFORMATION: Tyr, Val, Ser or Ala
<220> FEATURE:
<221> NAME/KEY: MISC_FEATURE
<222> LOCATION: (198)..(209)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (200)..(200)
<223> OTHER INFORMATION: Tyr, Val, Ser or Ala
<220> FEATURE:
<221> NAME/KEY: MOD_RES
<222> LOCATION: (203)..(203)
<223> OTHER INFORMATION: Tyr, Val, Ser or Ala
<220> FEATURE:
<221> NAME/KEY: MOD_RES
<222> LOCATION: (206)..(206)
<223> OTHER INFORMATION: Tyr, Val, Ser or Ala
<220> FEATURE:
<221> NAME/KEY: MOD_RES
<222> LOCATION: (209)..(209)
<223> OTHER INFORMATION: Tyr, Val, Ser or Ala
<220> FEATURE:
<221> NAME/KEY: MISC_FEATURE
<222> LOCATION: (213)..(224)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (215)..(215)
<223> OTHER INFORMATION: Tyr, Val, Ser or Ala
<220> FEATURE:
<221> NAME/KEY: MOD_RES
<222> LOCATION: (218)..(218)
<223> OTHER INFORMATION: Tyr, Val, Ser or Ala
<220> FEATURE:
<221> NAME/KEY: MOD_RES
<222> LOCATION: (221)..(221)
<223> OTHER INFORMATION: Tyr, Val, Ser or Ala
<220> FEATURE:
<221> NAME/KEY: MOD_RES
<222> LOCATION: (224)..(224)
<223> OTHER INFORMATION: Tyr, Val, Ser or Ala
<220> FEATURE:
<221> NAME/KEY: MISC_FEATURE
<222> LOCATION: (228)..(239)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (230)..(230)
<223> OTHER INFORMATION: Tyr, Val, Ser or Ala
<220> FEATURE:
<221> NAME/KEY: MOD_RES
<222> LOCATION: (233)..(233)
<223> OTHER INFORMATION: Tyr, Val, Ser or Ala
<220> FEATURE:
<221> NAME/KEY: MOD_RES
<222> LOCATION: (236)..(236)
<223> OTHER INFORMATION: Tyr, Val, Ser or Ala
<220> FEATURE:
<221> NAME/KEY: MOD_RES
<222> LOCATION: (239)..(239)
<223> OTHER INFORMATION: Tyr, Val, Ser or Ala
<220> FEATURE:
<221> NAME/KEY: MISC_FEATURE
<222> LOCATION: (243)..(254)
<223> OTHER INFORMATION: This region may encompass 1-4 'Gly Gly Xaa'
      repeating units, wherein one or more repeat or all repeats are
```

```
      absent or present.
<220> FEATURE:
<221> NAME/KEY: MOD_RES
<222> LOCATION: (245)..(245)
<223> OTHER INFORMATION: Tyr, Val, Ser or Ala
<220> FEATURE:
<221> NAME/KEY: MOD_RES
<222> LOCATION: (248)..(248)
<223> OTHER INFORMATION: Tyr, Val, Ser or Ala
<220> FEATURE:
<221> NAME/KEY: MOD_RES
<222> LOCATION: (251)..(251)
<223> OTHER INFORMATION: Tyr, Val, Ser or Ala
<220> FEATURE:
<221> NAME/KEY: MOD_RES
<222> LOCATION: (254)..(254)
<223> OTHER INFORMATION: Tyr, Val, Ser or Ala
<220> FEATURE:
<221> NAME/KEY: MISC_FEATURE
<222> LOCATION: (258)..(269)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (260)..(260)
<223> OTHER INFORMATION: Tyr, Val, Ser or Ala
<220> FEATURE:
<221> NAME/KEY: MOD_RES
<222> LOCATION: (263)..(263)
<223> OTHER INFORMATION: Tyr, Val, Ser or Ala
<220> FEATURE:
<221> NAME/KEY: MOD_RES
<222> LOCATION: (266)..(266)
<223> OTHER INFORMATION: Tyr, Val, Ser or Ala
<220> FEATURE:
<221> NAME/KEY: MOD_RES
<222> LOCATION: (269)..(269)
<223> OTHER INFORMATION: Tyr, Val, Ser or Ala
<220> FEATURE:
<221> NAME/KEY: MISC_FEATURE
<222> LOCATION: (273)..(284)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (275)..(275)
<223> OTHER INFORMATION: Tyr, Val, Ser or Ala
<220> FEATURE:
<221> NAME/KEY: MOD_RES
<222> LOCATION: (278)..(278)
<223> OTHER INFORMATION: Tyr, Val, Ser or Ala
<220> FEATURE:
<221> NAME/KEY: MOD_RES
<222> LOCATION: (281)..(281)
<223> OTHER INFORMATION: Tyr, Val, Ser or Ala
<220> FEATURE:
<221> NAME/KEY: MOD_RES
<222> LOCATION: (284)..(284)
<223> OTHER INFORMATION: Tyr, Val, Ser or Ala
<220> FEATURE:
<221> NAME/KEY: MISC_FEATURE
<222> LOCATION: (288)..(299)
<223> OTHER INFORMATION: This region may encompass 1-4 'Gly Gly Xaa'
      repeating units, wherein one or more repeat or all repeats are
      absent or present.
<220> FEATURE:
<221> NAME/KEY: MOD_RES
<222> LOCATION: (290)..(290)
<223> OTHER INFORMATION: Tyr, Val, Ser or Ala
<220> FEATURE:
<221> NAME/KEY: MOD_RES
<222> LOCATION: (293)..(293)
<223> OTHER INFORMATION: Tyr, Val, Ser or Ala
<220> FEATURE:
<221> NAME/KEY: MOD_RES
<222> LOCATION: (296)..(296)
<223> OTHER INFORMATION: Tyr, Val, Ser or Ala
```

<220> FEATURE:
<221> NAME/KEY: MOD_RES
<222> LOCATION: (299)..(299)
<223> OTHER INFORMATION: Tyr, Val, Ser or Ala

<400> SEQUENCE: 10

```
Gly Pro Gly Gly Xaa Gly Gly Xaa Gly Gly Xaa Gly Gly Xaa Tyr Gly
1               5                   10                  15
Pro Gly Gly Xaa Gly Gly Xaa Gly Gly Xaa Gly Gly Xaa Tyr Gly Pro
                20                  25                  30
Gly Gly Xaa Gly Gly Xaa Gly Gly Xaa Gly Gly Xaa Tyr Gly Pro Gly
            35                  40                  45
Gly Xaa Gly Gly Xaa Gly Gly Xaa Gly Gly Xaa Tyr Gly Pro Gly Gly
        50                  55                  60
Xaa Gly Gly Xaa Gly Gly Xaa Gly Gly Xaa Tyr Gly Pro Gly Gly Xaa
65                  70                  75                  80
Gly Gly Xaa Gly Gly Xaa Gly Gly Xaa Tyr Gly Pro Gly Gly Xaa Gly
                85                  90                  95
Gly Xaa Gly Gly Xaa Gly Gly Xaa Tyr Gly Pro Gly Gly Xaa Gly Gly
            100                 105                 110
Xaa Gly Gly Xaa Gly Gly Xaa Tyr Gly Pro Gly Gly Xaa Gly Gly Xaa
        115                 120                 125
Gly Gly Xaa Gly Gly Xaa Tyr Gly Pro Gly Gly Xaa Gly Gly Xaa Gly
130                 135                 140
Gly Xaa Gly Gly Xaa Tyr Gly Pro Gly Gly Xaa Gly Gly Xaa Gly Gly
145                 150                 155                 160
Xaa Gly Gly Xaa Tyr Gly Pro Gly Gly Xaa Gly Gly Xaa Gly Gly Xaa
                165                 170                 175
Gly Gly Xaa Tyr Gly Pro Gly Gly Xaa Gly Gly Xaa Gly Gly Xaa Gly
            180                 185                 190
Gly Xaa Tyr Gly Pro Gly Gly Xaa Gly Gly Xaa Gly Gly Xaa Gly Gly
        195                 200                 205
Xaa Tyr Gly Pro Gly Gly Xaa Gly Gly Xaa Gly Gly Xaa Gly Gly Xaa
210                 215                 220
Tyr Gly Pro Gly Gly Xaa Gly Gly Xaa Gly Gly Xaa Gly Gly Xaa Tyr
225                 230                 235                 240
Gly Pro Gly Gly Xaa Gly Gly Xaa Gly Gly Xaa Gly Gly Xaa Tyr Gly
                245                 250                 255
Pro Gly Gly Xaa Gly Gly Xaa Gly Gly Xaa Gly Gly Xaa Tyr Gly Pro
            260                 265                 270
Gly Gly Xaa Gly Gly Xaa Gly Gly Xaa Gly Gly Xaa Tyr Gly Pro Gly
        275                 280                 285
Gly Xaa Gly Gly Xaa Gly Gly Xaa Gly Gly Xaa Tyr
290                 295                 300
```

<210> SEQ ID NO 11
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (8)..(24)
<223> OTHER INFORMATION: Ala or absent

<400> SEQUENCE: 11

Gly Arg Gly Gly Ala Ala Ala Xaa Xaa Xaa Xaa Xaa Xaa Xaa Xaa Xaa

```
                1               5                  10                 15
Xaa Xaa Xaa Xaa Xaa Xaa Xaa Xaa
            20

<210> SEQ ID NO 12
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (10)..(10)
<223> OTHER INFORMATION: Ala or absent

<400> SEQUENCE: 12

Gly Ala Gly Ala Ala Ala Ala Ala Ala Xaa Gly Gly Ala
1               5                   10

<210> SEQ ID NO 13
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (3)..(3)
<223> OTHER INFORMATION: Gln, Tyr, Leu, Ala, Ser or Arg
<220> FEATURE:
<221> NAME/KEY: MOD_RES
<222> LOCATION: (5)..(5)
<223> OTHER INFORMATION: Gln, Tyr, Leu, Ala, Ser or Arg
<220> FEATURE:
<221> NAME/KEY: MOD_RES
<222> LOCATION: (7)..(8)
<223> OTHER INFORMATION: Gln, Tyr, Leu, Ala, Ser or Arg

<400> SEQUENCE: 13

Gly Gly Xaa Gly Xaa Gly Xaa Xaa
1               5

<210> SEQ ID NO 14
<211> LENGTH: 16
<212> TYPE: PRT
<213> ORGANISM: Artificial Sequence
<220> FEATURE:
<223> OTHER INFORMATION: synthetic

<400> SEQUENCE: 14

Thr Gly Ser Ser Gly Phe Gly Pro Tyr Val Asn Gly Gly Tyr Ser Gly
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: synthetic

<400> SEQUENCE: 15

Tyr Glu Tyr Ala Trp Ser Ser Glu
1               5

<210> SEQ ID NO 16
<211> LENGTH: 7
<212> TYPE: PRT
<213> ORGANISM: Artificial Sequence
<220> FEATURE:
```

<223> OTHER INFORMATION: synthetic

<400> SEQUENCE: 16

Ser Asp Phe Gly Thr Gly Ser
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic

<400> SEQUENCE: 17

Arg Arg Ala Gly Tyr Asp Arg
1               5

<210> SEQ ID NO 18
<211> LENGTH: 8
<212> TYPE: PRT
<213> ORGANISM: Artificial Sequence
<220> FEATURE:
<223> OTHER INFORMATION: synthetic

<400> SEQUENCE: 18

Glu Val Ile Val Ile Asp Asp Arg
1               5

<210> SEQ ID NO 19
<211> LENGTH: 18
<212> TYPE: PRT
<213> ORGANISM: Artificial Sequence
<220> FEATURE:
<223> OTHER INFORMATION: synthetic

<400> SEQUENCE: 19

Thr Thr Ile Ile Glu Asp Leu Asp Ile Thr Ile Asp Gly Ala Asp Gly
1               5                   10                  15

Pro Ile

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Thr Ile Ser Glu Glu Leu Thr Ile
1               5

<210> SEQ ID NO 21

<400> SEQUENCE: 21

000

<210> SEQ ID NO 22
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(5)
<223> OTHER INFORMATION: Any amino acid

```
<400> SEQUENCE: 22

Gly Pro Gly Xaa Xaa
1               5

<210> SEQ ID NO 23
<211> LENGTH: 3
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (3)..(3)
<223> OTHER INFORMATION: Leu, Tyr or Ile

<400> SEQUENCE: 23

Gly Pro Xaa
1

<210> SEQ ID NO 24
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (3)..(22)
<223> OTHER INFORMATION: Ala, Thr, Val, Ser or absent
<220> FEATURE:
<221> NAME/KEY: MISC_FEATURE
<222> LOCATION: (3)..(22)
<223> OTHER INFORMATION: Any one or all of amino acids 3-22 can either
      absent or present.

<400> SEQUENCE: 24

Gly Gly Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 25
<211> LENGTH: 6
<212> TYPE: PRT
<213> ORGANISM: Artificial Sequence
<220> FEATURE:
<223> OTHER INFORMATION: synthetic

<400> SEQUENCE: 25

Gly Ala Gly Ala Gly Ser
1               5
```